United States Patent
Lau et al.

(10) Patent No.: US 11,725,073 B2
(45) Date of Patent: Aug. 15, 2023

(54) COMPOSITIONS AND METHODS FOR LIQUID PHASE OLIGONUCLEOTIDE SYNTHESIS

(71) Applicant: Hongene Biotech Corporation, Union City, CA (US)

(72) Inventors: Aldrich N. K. Lau, Palo Alto, CA (US); Xiaoyang Guan, Fremont, CA (US); David Yu, Union City, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 17/562,714

(22) Filed: Dec. 27, 2021

(65) Prior Publication Data

US 2022/0204670 A1 Jun. 30, 2022

Related U.S. Application Data

(60) Provisional application No. 63/131,449, filed on Dec. 29, 2020.

(51) Int. Cl.
```
C07H 19/00    (2006.01)
C07H 21/02    (2006.01)
A61K 47/54    (2017.01)
A61K 47/58    (2017.01)
C08F 220/22   (2006.01)
```

(52) U.S. Cl.
CPC .......... *C08F 220/22* (2013.01); *A61K 47/549* (2017.08); *A61K 47/58* (2017.08); *C07H 19/00* (2013.01); *C07H 21/02* (2013.01)

(58) Field of Classification Search
CPC .............................. C07H 19/00; C07H 21/02
See application file for complete search history.

(56) References Cited

U.S. PATENT DOCUMENTS

| | | | |
|---|---|---|---|
| 5,798,210 | A | 8/1998 | Canard et al. |
| 6,677,120 | B2 | 1/2004 | Sanghvi et al. |
| 7,276,599 | B2 | 10/2007 | Moore et al. |
| 8,143,369 | B2 | 3/2012 | Fujiwara et al. |
| 8,450,504 | B2 | 5/2013 | Hedrick et al. |
| 8,664,357 | B2 | 3/2014 | Livingston |
| 10,544,456 | B2 | 1/2020 | Esfandyarpour et al. |
| 2013/0231260 | A1 | 9/2013 | Lau et al. |
| 2014/0287945 | A1 | 9/2014 | Lau et al. |
| 2018/0023122 | A1 | 1/2018 | Crameri et al. |
| 2018/0100190 | A1 | 4/2018 | Esfandyarpour et al. |

FOREIGN PATENT DOCUMENTS

| | | |
|---|---|---|
| EP | 0 850 949 | 7/1998 |
| EP | 1 710 249 | 1/2005 |
| FR | 2623510 | 5/1989 |
| WO | WO 02/079215 | 10/2002 |
| WO | WO 03/093346 | 11/2003 |
| WO | WO 05/123139 | 12/2005 |
| WO | WO-2016160475 A1 * | 10/2016 .......... B01J 19/0046 |

OTHER PUBLICATIONS

Bonora et al., Nucleic Acids Research, 1993, 21(5), p. 1213-1217. (Year: 1993).*
Gravert et al., Chem. Rev., 1997, 97, p. 489-509. (Year: 1997).*
Wang et al., Progress in Polymer Science, 2016, 53, p. 169-206. (Year: 2016).*
Atdbio, 2021, Solid State Oligonucleotide Synthesis, https://www.atdbio.com/content/17/Solid-phase-oligonucleotide-synthesis, 26 pp.
Beaucage et al., 1992, Advances in the synthesis of oligonucieotides by the phosphoramidite approach, Tetrahedron, 48(12):2223-2311.
Carey, 1992, Organic Chemistry, 2d ed., McGraw-Hill, Inc., New York, pp. 328-331.
Creusen et al., 2020, Scalable one-pot—liquid-phase oligonucleotide synthesis for model network hydrogels, ChemRxiv., preprint. https://doi.org/10.26434/chemrxiv.12327569.v1.
Gorelov et al., 1979, Thermal decomposition of poly(pheny/- and poly(pentafluorophenyl acrylates)), Vysokomoiekularnye Soedineniya, Seriya B: Bratkie Soobshcheniya, 21(6):410-413 (abstract).
Greene et al., 1999, Protective Groups in Organic Synthesis, 3rd Ed., John Wiley & Sons, New York (TOC).
Katayama et al., 2018, Liquid-phase synthesis of oligonucleotides, in Synthesis of Therapeutic Oligonucleotides, Obika et al., eds., Springer Nature Singapore Pte Ltd., pp. 83-95.
Kim et al., 2013, Liquid-phase RNA synthesis by using alkyl-chain-soluble support, Chem. Eur. J., 19:8615-8620.
Livingston, Jan. 2, 2020, Liquid phase oligonucleotide synthesis, Oxford Global, Biologies Series, 2 pp.
McMurry, 2000, Organic Chemistry, 5th ed., Brooks/Cole, Pacific Grove, CA, pp. 398 and 408.
McOmie, ed., 1973, Protective Groups in Organic Chemistry, Plenum Press (TOC).
Merrifield, Jul. 20, 1963, Solid phase peptide synthesis. I. The synthesis of a tetrapeptide, J. Am. Chem. Soc., 85(14):2149-2154.
Merrifield, Oct. 8, 1965, Automated synthesis of peptides: solid-phase peptide synthesis, a simple and rapid synthetic method, has now been automates, Science, 150(3693):178-185.
Molina et al., 2019, Liquid-phase oligonucleotide synthesis: past, present, and future predictions, Current Protocols in Nucleic Acid Chemistry, 77:e82, 17 pp.
Scheit, 1980. Nucleotide analogs: Synthesis and biological function. New York: John Wiley & Sons (TOC).
Streitwieser et al., 1981, Introduction to Organic Chemistry, 2d ed., Macmillan Publishing Co., Inc., New York, pp. 169-171.
Takahashi et al., 2012, Development of an efficient liquid-phase peptide synthesis protocol using a novel fluorene-derived anchor support compound with Fmoc chemistry; AJIPHASE®, Tetrahedron Lett., 53:1936-1939.
Takahashi et al., 2012, Novel diphenylmethyl-derived amide protecting group for efficient liquid-phase peptide synthesis: AJIPHASE, Organic Lett., 14:4514-4517.

(Continued)

*Primary Examiner* — Jonathan S Lau
(74) *Attorney, Agent, or Firm* — Knobbe, Martens, Olson & Bear LLP

(57) ABSTRACT

Embodiments of the present application relate to polymers for liquid phase oligonucleotide synthesis. Methods for making an oligonucleotide by liquid phase oligonucleotide synthesis, comprising dissolving a polyvalent hub having a plurality of functional groups in a solvent and contacting the polyvalent hub with one or more nucleoside analogs to form a first bioconjugate are also provided.

31 Claims, 8 Drawing Sheets

(56) References Cited

OTHER PUBLICATIONS

Takahashi et al., 2017, AJIPHASE®: a highly efficient synthetic method for one-pot peptide elongation in the solution phase by an Fmoc strategy, Angew. Chem. Int. Ed., 56:7803-7807.
Uhlman et al., Jun. 1990, Antisense oligonucleotides: a new therapeutic principle, Chemical Reviews, 90(4):543-584.

* cited by examiner

COMPOSITIONS AND METHODS FOR LIQUID PHASE OLIGONUCLEOTIDE SYNTHESIS

INCORPORATION BY REFERENCE TO ANY PRIORITY APPLICATION

The present application claims the benefit of priority to U.S. Provisional Application No. 63/131,449, filed Dec. 29, 2020, which is incorporated by reference in its entirety.

BACKGROUND

Field

The present application relates to methods and compositions for liquid phase oligonucleotide synthesis employing the use of a polyvalent polymer hub.

Description of the Related Art

Oligonucleotide-based drugs have become a powerful epitome having ability to treat various diseases. Currently, the demand for oligonucleotides can be fulfilled by conventional solid phase oligonucleotide synthesis. There are certain advantages of Solid Phase Oligo Synthesis (SPOS), such as simple product isolation and the use of anhydrous synthetic environment. However, the SPOS generally has low over all yield after multiple steps for an oligo sequence and high cost for reagents, solid support and waste management. In addition, SPOS may result in mismatched oligo sequences which leads to difficulty in purification. The increasing demand for metric ton quantities of oligonucleotides far exceeds the production capacity of solid phase oligonucleotide synthesis.

Liquid phase oligonucleotide synthesis (LPOS) is a technology with the potential to provide the production capacity that will be required. One of the major advantages of LPOS over SPOS is the absence of the heterogeneous nature of the process, i.e., insoluble solid supports are not present. The use of a soluble scaffold or support employed in LPOS allows each step of the synthesis to be performed in the liquid phase.

The recent advances in the LPOS have been reported by Molina et al., *Current Protocol in Nucleic Acid Chemistry* (2019) 77, e82. The current LPOS technologies have an unfavorable E factor and additional efforts are required to address the usage of excessive reagents and solvents. In addition, one of the current challenges of LPOS is the difficulties associated in isolating and purifying the oligonucleotide products. For example, the nanofiltration technologies currently employed for isolation and purification are not economically favorable. There exists a need for improved materials and methods for conducting liquid phase oligonucleotide synthesis, for example, the need to expand the current repertoire of soluble supports with increased solubility and lower costs, while allowing for efficient removal of excess reagents and protecting groups after each LPOS cycle using a minimum amount of solvent.

SUMMARY

Some aspect of the present disclosure relates to a method for making oligonucleotides by liquid phase oligonucleotide synthesis (LPOS), comprising:

dissolving a polyvalent hub (PVH) in a first solvent to form a reaction matrix, the PVH comprises or is an acrylate polymer having a plurality of reactive ester groups capable of reacting with nucleoside or nucleotide analogs (i.e., anchor groups); and contacting the PVH with one or more nucleoside analogs to form a first bioconjugate comprising a structure of Formula (I):

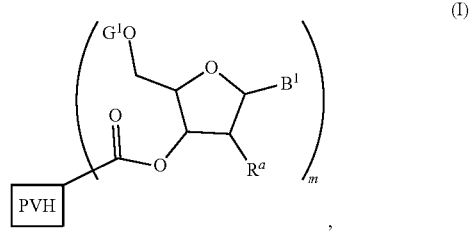

wherein $B^1$ is a nitrogenous base;

$G^1$ is a 5' hydroxyl blocking group;

$R^a$ is —H, —OH, halogen, —O—($C_1$-$C_6$ alkyl), —O—($C_1$-$C_6$ haloalkyl), or —OX, where X is a 2' hydroxyl protecting group; and m is an integer from 1 to about 500,000.

In some embodiments, the PVH used in the method comprises or is a homopolymer of the acrylate polymer. In other embodiments, the PVH is a random copolymer of a reactive vinyl monomer (e.g., an acrylate monomer containing reactive ester functional group) and an acrylamide monomer.

In some embodiments of the method described herein, the formation of the first bioconjugate described in the method does not require a succinate linker to attach the nucleoside analog to the PVH.

In some embodiments, the method further comprises removing the 5' blocking group ($G^1$) to form a 5' unblocked first bioconjugate; and isolating the 5' unblocked first bioconjugate. In some embodiments, the 5' unblocked first bioconjugate comprises the structure of Formula (I'):

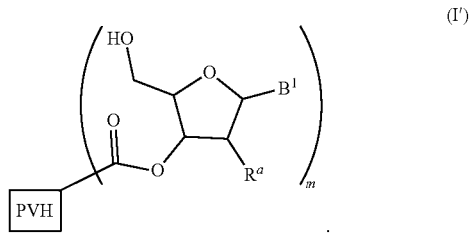

In some further embodiments, the method further comprises:

(a) reacting the 5' unblocked first bioconjugate with one or more nucleoside phosphoramidite analogs in a second solvent to form a second bioconjugate comprising the structure of Formula (IV):

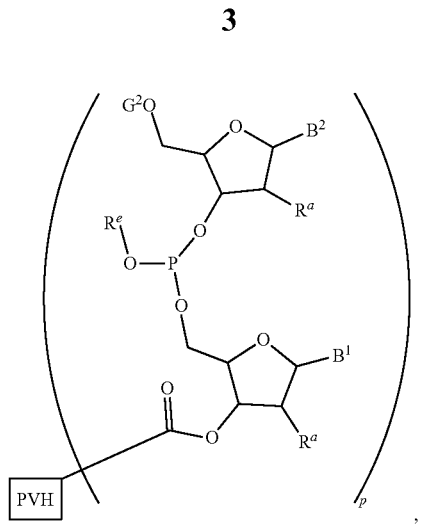

(IV)

wherein
- $G^2$ is a 5' hydroxyl blocking group;
- $B^2$ is a nitrogenous base;
- $R^e$ is a phosphite protecting group; and
- p is an integer of 1 to about 500,000;

(b) oxidizing the phosphite moiety in Formula (IV);

(c) removing the 5' blocking group $G^2$ to form a 5' unblocked second bioconjugate comprising the structure of Formula (IV'):

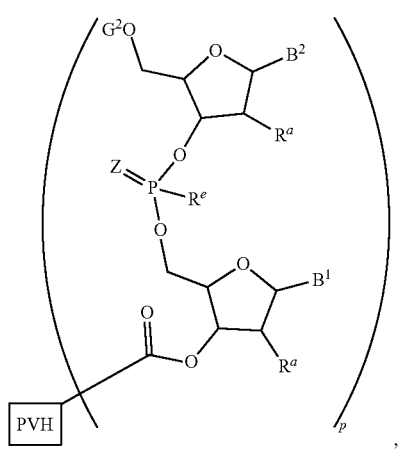

(IV')

wherein Z is O or S; and (d) isolating the 5' unblocked second bioconjugate. In some embodiments, steps (a)-(d) are repeated multiple cycles until a desired length of oligonucleotide has been synthesized.

Some other aspect of the present disclosure relates to oligonucleotides synthesized by the liquid phase oligo synthesis method described herein, wherein the oligonucleotides have at least 2, 3, 4, 5, 6, 7, 8, 9, 10, 15 or 20 bases.

Some further aspect of the present disclosure relates to the polyvalent hub (PVH) used for the liquid phase oligonucleotide synthesis described herein, wherein the PVH comprises or is an acrylate polymer comprising repeating units of Formula (II) or (II'):

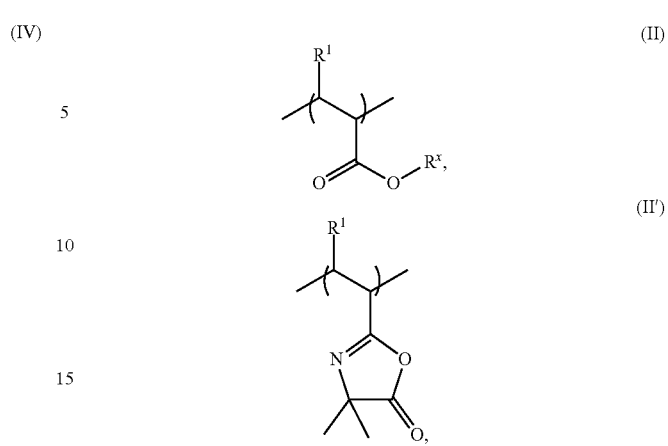

(II)

(II')

wherein $R^1$ is H or $C_1$-$C_6$ alkyl; $R^x$ is

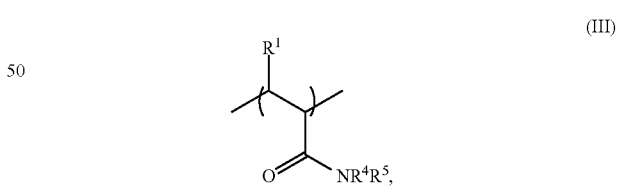

each $R^2$ is independently halogen, nitro or cyano; and n is 1, 2, 3, 4, or 5. In some embodiments, the PVH may further comprise acrylamide repeating units or other acrylate repeating units that do not have reactive groups for attaching nucleoside or nucleotide analogs. In some further embodiment, the PVH comprises or is a copolymer, comprising one or more acrylate repeating units of Formula (II) or (II') as described herein, or a combination thereof, and one or more acrylamide repeating units of Formula (III):

(III)

wherein $R^3$ is H or $C_1$-$C_6$ alkyl; each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl. In some embodiments, the number of the acrylate repeating unit is x, and the number of acrylamide repeating unit is y, where each x and y is independently an integer of 1 to 500,000.

In some embodiments of the copolymer PVH, the copolymer comprises the structure:

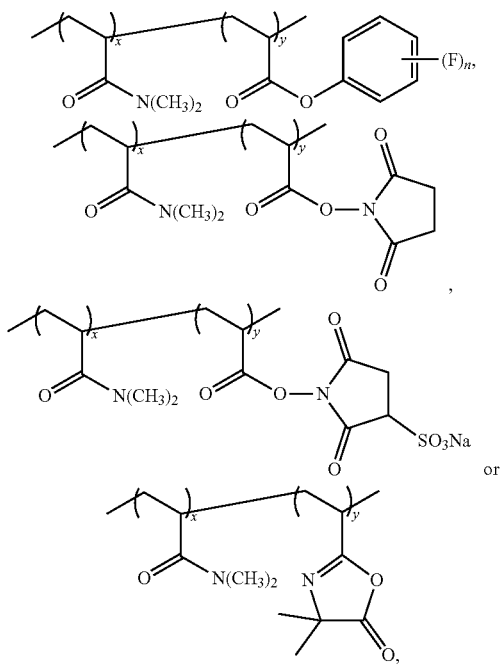

wherein each of x and y is independently an integer from 1 to 500,000; and n is 4 or 5.

Some additional aspect of the present disclosure relates to a polymeric bioconjugate for liquid phase oligonucleotide synthesis, said polymeric bioconjugate comprising one or more repeating units of Formula (V):

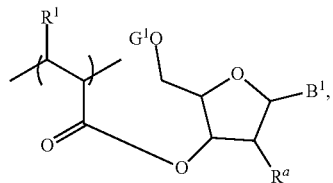

and optionally one or more repeating unit of formula (III):

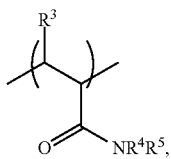

wherein
each of $R^1$ and $R^3$ is independently H or $C_1$-$C_6$ alkyl;
each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl;
$B^1$ is a nitrogenous base;
$G^1$ is a 5' hydroxyl blocking group; and
$R^a$ is —H, —OH, halogen, —O—($C_1$-$C_6$ alkyl), —O—($C_1$-$C_6$ haloalkyl), or —OX, where X is a 2' hydroxyl protecting group. In further embodiments, the polymeric bioconjugate comprises or has the structure of Formula (Ia):

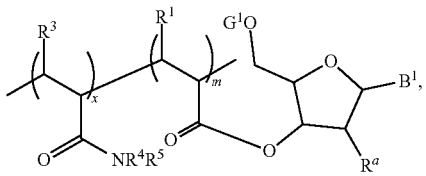

wherein each of x and m is independently an integer from 1 to about 500,000. In some further embodiments, m is less than y.

Additional aspect of the present disclosure relate to a polymeric bioconjugate for liquid phase oligonucleotide synthesis, comprising one or more repeating units of Formula (VI):

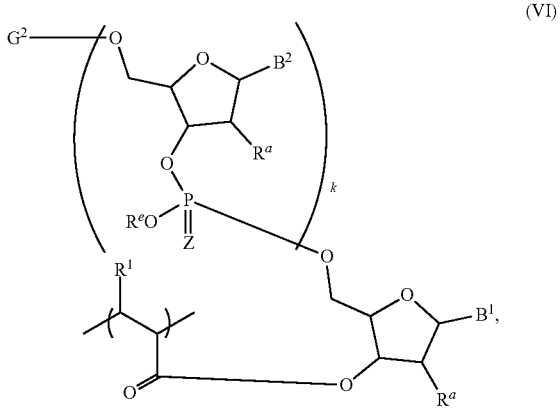

and optionally one or more repeating unit of formula (III):

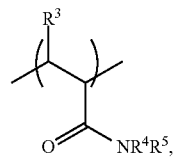

wherein
each of $R^1$ and $R^3$ is independently H or $C_1$-$C_6$ alkyl;
each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl;
$R^a$ is —H, —OH, halogen, —O—($C_1$-$C_6$ alkyl), —O—($C_1$-$C_6$ haloalkyl), or —OX, where X is a 2' hydroxyl protecting group.
each of $B^1$ and $B^2$ is independently a nitrogenous base;
$G^2$ is a 5' hydroxyl blocking group;
$R^e$ is unsubstituted or substituted $C_1$-$C_6$ alkyl;
Z is O or S; and
k is an integer from 1 to 500.
In further embodiments, the polymeric bioconjugate comprises or has the structure of Formula (Ib):

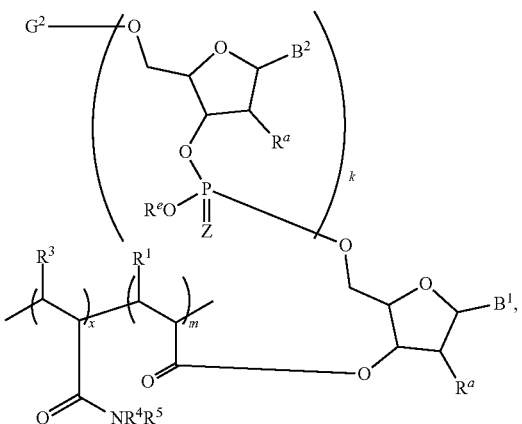

(Ib)

wherein each of x and m is independently an integer from 1 to about 500,000. In some further embodiments, m is equal to or less than y.

In any embodiments of the method, the PVH or the PVH containing bioconjugate described herein, the PVH may comprise or is a random copolymer having molecular weight ranging from about 10 kDa to about 1000 kDa, from about 20 KDa to about 500 KDa, or from about 30 kDa to about 100 kDa.

DETAILED DESCRIPTION

Figure 1:
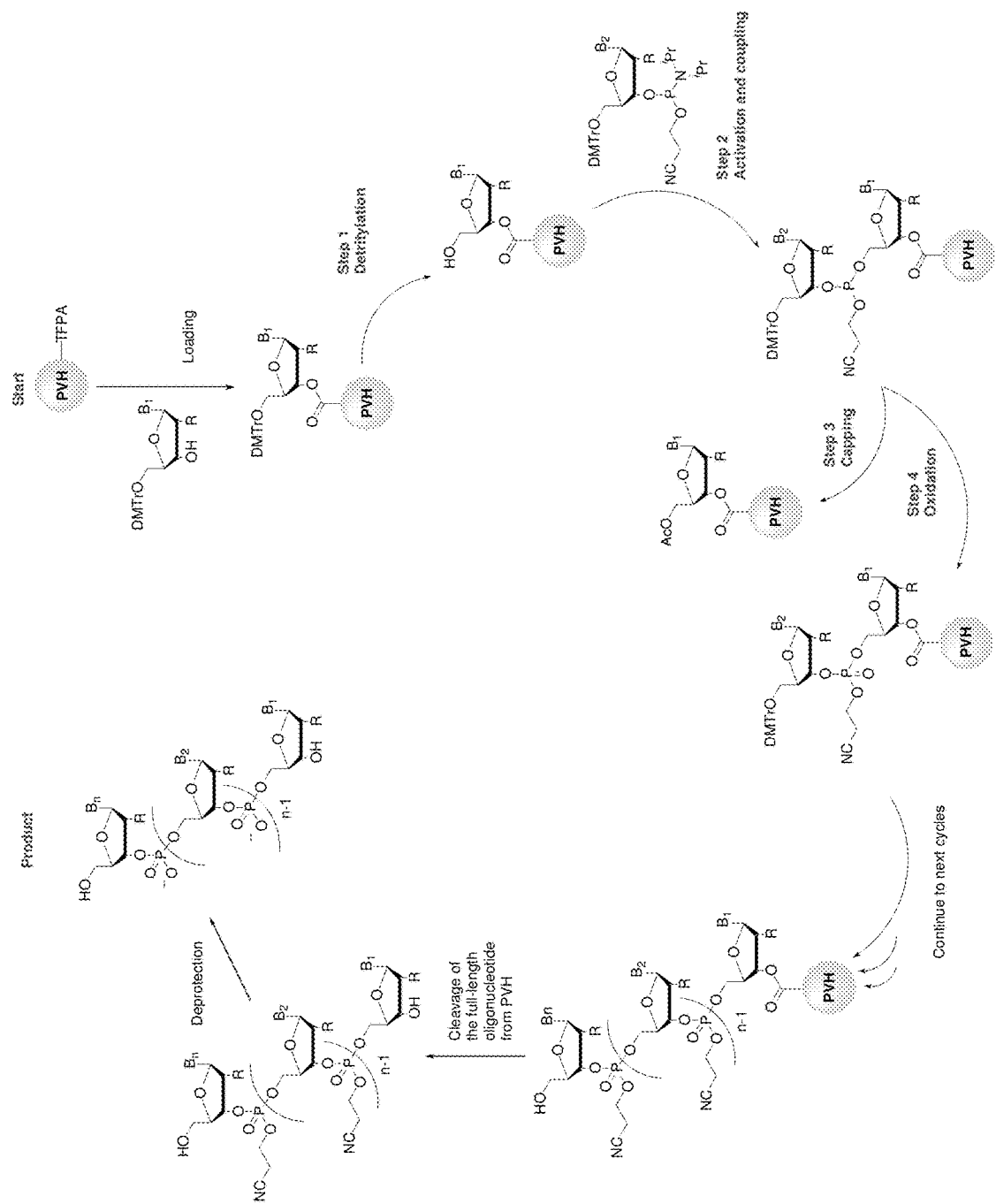
FIG. 1 is a general reaction scheme for making an oligonucleotide by liquid phase oligonucleotide synthesis according to an embodiment of the present application.

Solid phase oligonucleotide synthesis enable oligo synthesis at the solid support-liquid interface. The solid support is insoluble in the liquid medium (e.g., organic solvent). Examples of solid support include particles of controlled porous glass (CPG) and porous crosslink polystyrene. In contrast, liquid phase oligo synthesis (LPOS) relies on a soluble organic compound as support (hub) to carry out oligo synthesis in solution. Conventional LPOS typically utilizes soluble supports that have one or several functional groups as anchors to conjugate and synthesize oligos. Embodiments of the present disclosure relate to methods for liquid phase oligonucleotide synthesis by using a polymeric soluble hub (i.e., polyvalent hub or PVH) that has numerous functional groups along the polymer chain for oligo synthesis. For example, the PVH described herein may contain reactive ester groups that allows for efficient conjugation with nucleoside or nucleotide analogs with improved yield compared to known liquid phase oligonucleotide synthesis and solid phase oligonucleotide synthesis. Furthermore, the PVH of the present disclosure eliminates the use of succinate linker to attach the nucleoside or nucleotide analogs to the PVH. The methods also utilize regenerated cellulose membrane to isolate and purify the growing oligo bioconjugates after each cycle of the synthesis. Regenerated cellulose membrane described herein is a cost-effective alternative to the nanofiltration technology used in the LPOS. The methods described herein is amenable for multi-kilogram oligonucleotide synthesis.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components. By "consisting of" is meant including, and limited to, whatever follows the phrase "consisting of." By "consisting essentially of" is meant including any elements listed after the phrase, and limited to other elements that do not interfere with or contribute to the activity or action specified in the disclosure for the listed elements.

As used herein, the term "average molecular weight" is the weight-average molecular weight (Mw) of a sample population made up of polymer species having a multiplicity of molecular weights. This quantity is defined by the equation:

$$M_w = \left(\sum_{i=1} n_i \times (M_i)^2\right) \bigg/ \sum_{i=1} n_i \times M_i$$

where $n_i$ indicates the number of molecules of species $i$ and $M_i$ is the molecular weight of $i^{th}$ species. As used herein, the term "molecular weight" refers to weight average molecular weight, unless otherwise specified.

As used herein, the term "polymer" used herein in its traditional sense, is a large molecule composed of smaller monomeric or oligomeric subunits covalently linked together to form a chain. A "homopolymer" is a polymer made up of only one monomeric repeating unit. A "copolymer" refers to a polymer made up of two or more kinds of monomeric repeating unit. Linear polymers are composed of monomeric subunits linked together in one continuous length to form polymer chains. Branched polymers are similar to linear polymers but have side chains protruding from various branch points along the main polymer. Star-shaped polymers are similar to branched polymers except that multiple side branches radiate from a single branch site, resulting in a star-shaped or wheel-and-spoke appearance.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$ alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a "cyano" group refers to a "—CN" group.

As used herein, a "nitro" group refers to a "—$NO_2$" group.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, sulfo, sulfino, sulfonate, and oxo (=O). Wherever a group is described as "optionally substituted" that group can be substituted with the above substituents.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g., 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

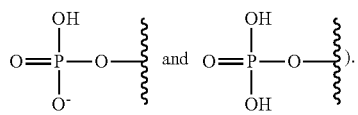

As used herein, the terms "monophosphate," "diphosphate," and "triphosphate" are used in their ordinary sense as understood by those skilled in the art, and include protonated forms.

As used herein, the terms "protecting group" and "blocking group" refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

As used herein, the term "reactive ester" refers to either an acyclic or a cyclic ester functional group comprising the moiety —C(=O)O— that is highly susceptible toward nucleophilic attack.

As used herein, "loading capacity" or "load" is expressed in mmol or μmol of a nucleoside bound to the polyvalent hub (PVH) described herein per gram of PVH (i.e., mmol/g).

Method for Preparing an Oligonucleotide by LPOS

Some embodiments of the present application relate to a method for making a compound by liquid phase synthesis. The compound may be an oligonucleotide, a peptide, a polynucleotide (i.e., nucleic acid), or a small molecule. In certain embodiments, the method is for making an oligonucleotide by liquid phase oligonucleotide synthesis. In certain embodiments, the method is for making a peptide by liquid phase peptide synthesis. In certain embodiments, the method is for making a polynucleotide (i.e., nucleic acid) by liquid phase polynucleotide (i.e., nucleic acid) synthesis. In certain embodiments, the method is for making a small molecule by liquid phase small molecule synthesis. Embodiments of the method provided herein use a polyvalent hub (PVH) as alternative to a solid support for the synthesis.

In some embodiments of the method described herein, the method includes dissolving a polyvalent hub (PVH) in a first solvent to form a reaction matrix, contacting the PVH with one or more nucleoside analogs to form a first bioconjugate comprising a structure of Formula (I):

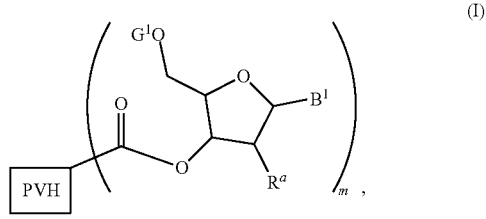

wherein $B^1$ is a nitrogenous base (such as purine, deazapurine or pyrimidine base); $G^1$ is a 5' hydroxyl blocking group; $R^a$ is —H, —OH, halogen, —O—(C$_1$-C$_6$ alkyl), —O—(C$_1$-

$C_6$ haloalkyl), or —OX, where X is a 2' hydroxyl protecting group; and m is an integer from 1 to 500,000. In some such embodiments, m is from 4 to about 50,000. In further embodiments, the number of m is at least 5, 10, 20, 30, 40, 50, 60, 70, 80, 90, 100, 200, 300, 400, 500, 600, 700, 800, 900, or 1000. The structure of Formula (I) illustrates the attachment of the 3' oxygen of the ribose ring of one or more nucleoside analogs to reactive sites of the PVH via an ester bond.

In some embodiments of the method described herein, $B^1$ is independently optionally protected adenine, optionally protected deaza adenine, optionally protected cytosine, optionally protected guanine, optionally protected deaza guanine, optionally protected thymine, or optionally protected uracil. In further embodiments, $B^1$ is

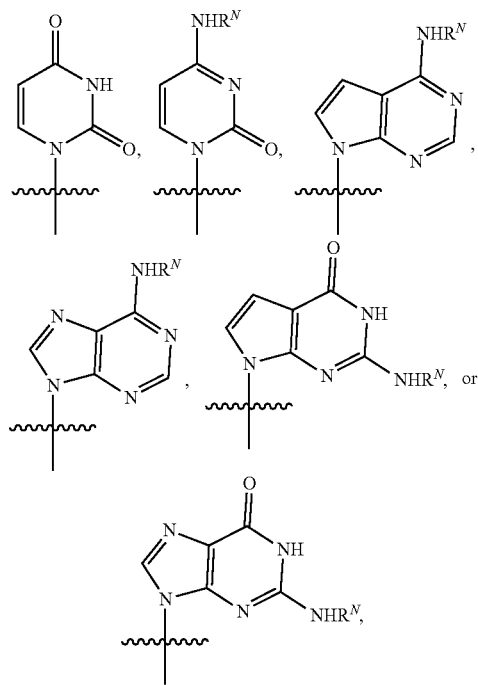

wherein $R^N$ is hydrogen, unsubstituted or substituted $C_1$-$C_6$ alkyl, or an amino protecting group, or the hydrogen in —$NHR^N$ is absent and $R^N$ is a divalent amino protecting group.

In some embodiments of the method described herein, each $G^1$ is independently a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl. In some such embodiments, each $G^1$ is independently

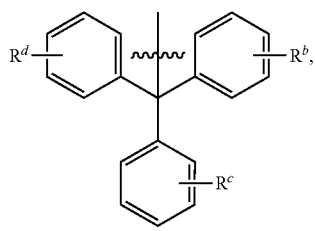

wherein each of $R^b$, $R^c$ and $R^d$ is independently H or $C_1$-$C_6$ alkoxy. In one embodiment, $G^1$ is bis(4-methoxyphenyl)phenylmethyl (4,4'-dimethoxytrityl).

In some embodiments, the PVH comprises or is an acrylate polymer having a plurality of reactive ester groups capable of reacting with nucleoside or nucleotide analogs. In some embodiments, each reactive ester group of the PVH independently comprises —C(=O)OEW, NHS ester (e.g.,

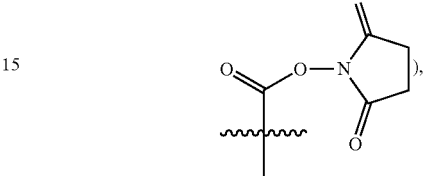

sulfo-NHS ester (e.g.,

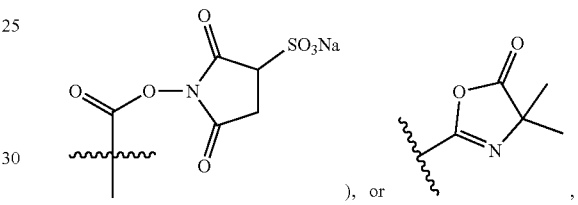

wherein EW is an electron-withdrawing group. In some embodiments, the PVH comprises —C(=O)—NH(CH$_2$)$_{2-5}$OH or C(=O)—NH(CH$_2$)$_{2-5}$NH$_2$. In other embodiments, the PVH does not comprise —C(=O)—NH(CH$_2$)$_{2-5}$OH or C(=O)—NH(CH$_2$)$_{2-5}$NH$_2$.

In some embodiments, the first bioconjugate described herein may include linkers between the reactive ester group the PVH and each of the nucleoside analogs. In some embodiments, the linkers comprise $C_2$-$C_6$ alkyl diamines, $C_2$-$C_6$ hydroxy alkylamines, —C(O)O— groups and combinations thereof. In some embodiments, the linkages comprise —C(O)O— groups. In some embodiments, the linkages do not include a succinate or derivatives thereof.

In any embodiments of the method described herein, the formation of the first bioconjugate does not require a succinate linker to attach the nucleoside analog to the PVH.

In some embodiments of the method described herein, the acrylate polymer of the PVH comprises a plurality of repeating units of Formula (II) or (II'):

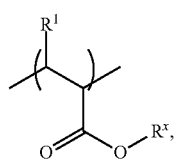

(II)

-continued

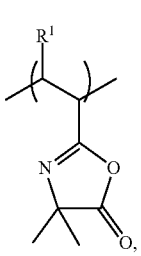

(II')

wherein $R^1$ is H or $C_1$-$C_6$ alkyl; $R^x$ is

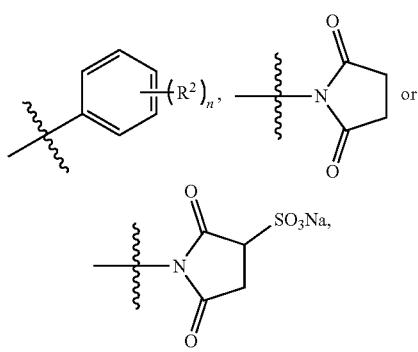

each $R^2$ is independently halogen, nitro or cyano; and n is 1, 2, 3, 4, or 5. In some such embodiments, $R^1$ is H or methyl. In some further embodiments, each $R^2$ is fluoro, and n is 3, 4, or 5. In one embodiment, the PVH comprise

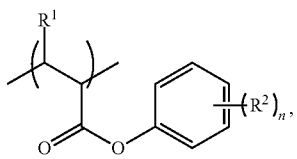

(IIa)

$R^1$ is H, each $R^2$ is fluoro, and n is 4.

In some further embodiments of the method described herein, the PVH comprises or is a copolymer comprising the acrylate polymer described herein and an acrylamide polymer. In some such embodiments, the acrylamide polymer of the PVH comprises comprising a plurality of repeating units of Formula (III):

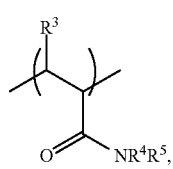

(III)

wherein $R^3$ is H or $C_1$-$C_6$ alkyl; and each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl. In some such embodiments, $R^3$ is H or methyl. In some embodiments, each $R^4$ and $R^5$ is independently unsubstituted $C_1$-$C_6$ alkyl. In one embodiment, $R^3$ is H and each $R^4$ and $R^5$ is methyl. In some embodiments, the molar ratio of the acrylate polymer to the acrylamide polymer in the copolymer is from about 1:200 to about 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, from about 5:1 to about 1:5; from about 2:1 to about 1:2; or about 1:1. In one embodiment, the molar ratio of the acrylate polymer to the acrylamide polymer in the copolymer is about 1:5. In some further embodiments, the PVH comprises the structure:

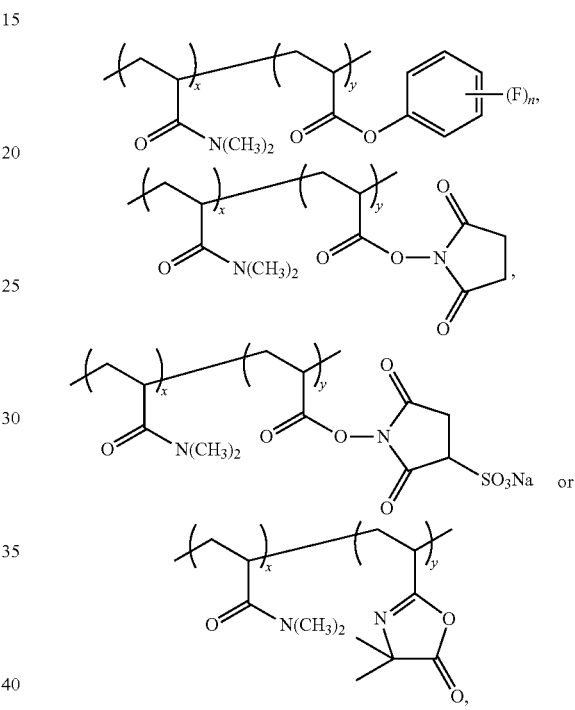

wherein x is an integer from 1 to 500,000; y is an integer from 1 to 500,000; and n is 4 or 5. The ratio of x:y may range from about 1:1000 to about 1000:1, from about 1:500 to about 500:1, from about 1:200 to about 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, or from about 1:5 to about 5:1. In some embodiments, the acrylate repeating units (y) in the copolymer is from about 0.1 mol % to about 100 mol %, form about 1 mol % to about 80 mol %, from about 5 mol % to about 60 mol %, or from about 10 mol % to about 50 mol %. In further embodiments, the number of acrylate repeating units (i.e., y) in the PVH is at least 5, 10, 20, 30, 40, 50, 60, 70, 80, 90, 100, 200, 300, 400, 500, 600, 700, 800, 900, or 1000.

In one embodiment, PVH comprises or is

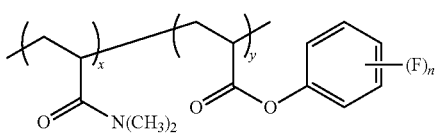

and n is 4, such copolymer of 2,3,5,6-tetrafluorophenyl acrylate (TFPA) and N,N-dimethyl acrylamide (DMA) can be referred to with the abbreviation poly(TFPA-co-DMA). In some embodiments, the acrylate repeating units (y) in the copolymer is from about 0.1 mol % to about 100 mol %, form about 1 mol % to about 80 mol %, from about 5 mol % to about 60 mol %, or from about 10 mol % to about 50 mol %. In one embodiment, the acrylate repeating units is about 15 to 20 mol %, or about 18 mol %.

In some embodiments of the method described herein, the PVH has an average molecular weight from about 10 kDa to about 1000 kDa, or from about 20 kDa to about 500 kDa, or from about 30 kDa to about 100 kDa. The PVH having an average molecular weight (MW) of about 30 KDa or higher extends into the bulk of the liquid phase, resulting in improved reaction kinetics and reaction yield. Furthermore, such PVH also facilitates rapid discharge of reaction debris and unreacted biomolecules having an average MW of about 2 K or less.

In some embodiments of the method described herein, the first bioconjugate comprises the structure of Formula (Ia):

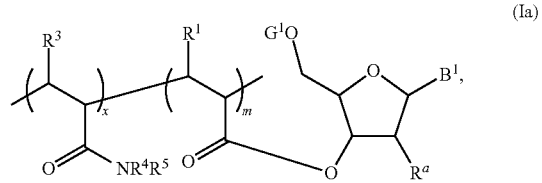

wherein x is an integer from 1 to 500,000; and m is an integer from 1 to 500,000. The first bioconjugate comprises a random or block copolymer of

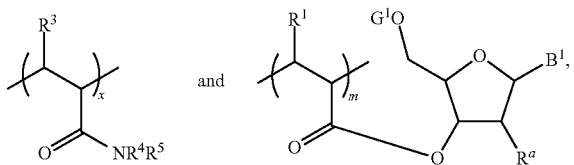

where m is equal or less than y as described herein. In some further embodiments, each of $R^1$ and $R^3$ is H and each of $R^4$ and $R^5$ is methyl. In further embodiments, the number of acrylate repeating units (i.e., y) is at least 5, 10, 20, 30, 40, 50, 60, 70, 80, 90, 100, 200, 300, 400, 500, 600, 700, 800, 900, or 1000.

In some embodiments of the method described herein, the method further comprising:

removing the 5' blocking group $G^1$ to form a 5' unblocked first bioconjugate; and isolating the 5' unblocked first bioconjugate;

wherein the 5' unblocked first bioconjugate comprises the structure of Formula (I'):

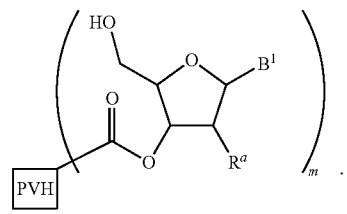

In some such embodiments, wherein the 5' unblocked bioconjugate comprises the structure of Formula (Ia'):

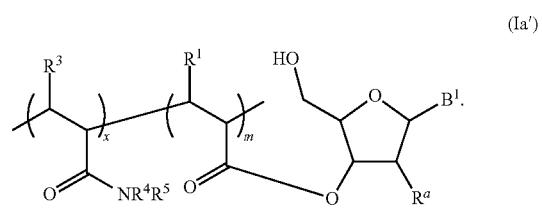

In some further embodiments, each of $R^1$ and $R^3$ is H and each of $R^4$ and $R^5$ is methyl.

In some embodiments of the method described herein, the isolation and/or purification of the 5' unblocked first bioconjugate is achieved by a filtration step. The filtration step may include dialysis, filtration, nanofiltration, ultrafiltration, any known filtration technology suitable for use herein and combinations thereof. In some embodiments, the filtration step comprises dialysis or filtration. In further embodiments, filtration step includes the use of a membrane. The membrane may comprise a cellulose acetate, a glass fiber, a carbon-based polymer, a regenerated cellulose and combinations thereof. In some embodiments, the regenerated cellulose membrane is negatively charged. In some embodiments, the regenerated cellulose comprises the structure:

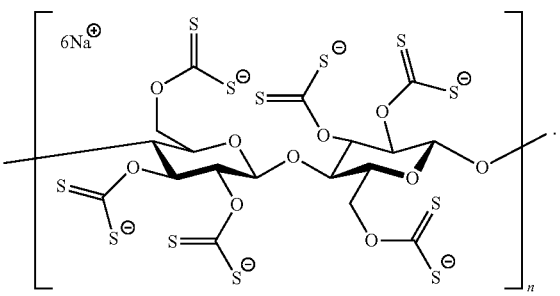

In some embodiments, the regenerated cellulose has a molecular weight cutoff (MWCO) from about 5 kDa to about 50 kDa, from about 6 kDa to about 40 kDa, about 7 kDa to about 30 kDa, or about 8 kDa to about 12 kDa. The regenerated cellulose membrane is capable of retain the PVH containing bioconjugate as an alternative to the expensive nanofiltration membranes prepared with polyimide. The negatively charged membrane capable of reducing non-specific adsorption of negatively charged biomolecules. In some embodiments, the regenerated cellulose is treated in a process including carbon disulfide followed by an aqueous metal hydroxide. In some embodiments, the regenerated cellulose comprises dithioate groups and metal cations. In some embodiments, the metal cations comprise group 1 metals (i.e., group IA metals or alkali metals), group 2 metals (i.e., group IIA metals or alkaline earth metals) and combinations thereof. In some embodiments, the metal cations comprise sodium cations. In certain embodiments, the regenerated cellulose has an electrostatic charge.

In some embodiments of the method described herein, the method further comprising:

(a) reacting the 5' unblocked first bioconjugate with one or more nucleoside phosphoramidite analogs in a second solvent to form a second bioconjugate comprising the structure of Formula (IV):

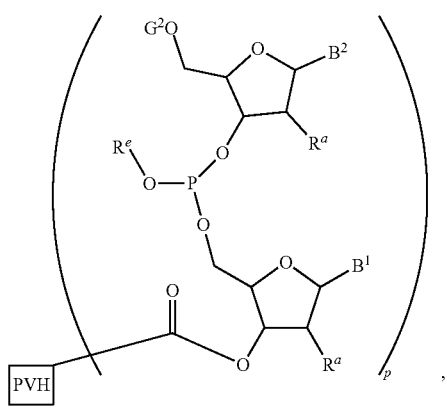
(IV)

wherein $G^2$ is a 5' hydroxyl blocking group; $B^2$ is a nitrogenous base (e.g., purine, deazapurine, or pyrimidine base); $R^e$ is a phosphite protecting group; and p is an integer of 1 to 500,000;

(b) oxidizing the phosphite moiety in Formula (IV);
(c) removing the 5' blocking group $G^2$ to form a 5' unblocked second bioconjugate comprising the structure of Formula (IV'):

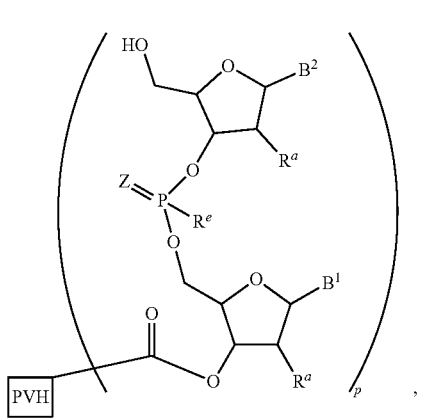
(IV')

wherein Z is O or S; and (d) isolating the 5' unblocked second bioconjugate. In some such embodiments, $B^2$ is independently optionally protected adenine, optionally protected deaza adenine, optionally protected cytosine, optionally protected guanine, optionally protected deaza guanine, optionally protected thymine, or optionally protected uracil. In further embodiments, $B^2$ is

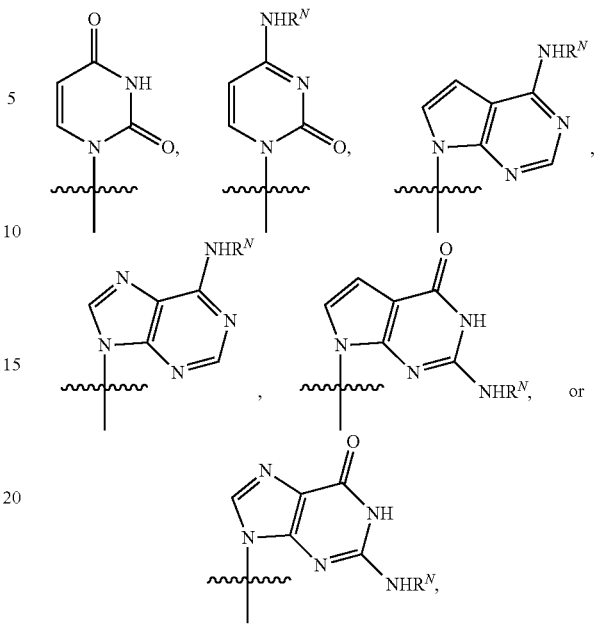

wherein $R^N$ is hydrogen, unsubstituted or substituted $C_1$-$C_6$ alkyl, or an amino protecting group, or the hydrogen in —NHR$^N$ is absent and $R^N$ is a divalent amino protecting group. In some embodiments, each $G^2$ is independently a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl. In some further embodiments, each $G^2$ is independently

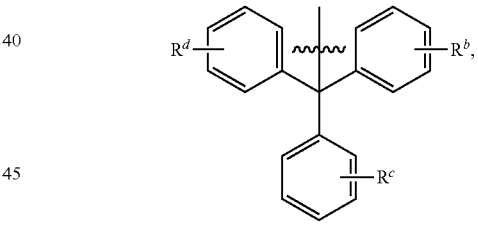

wherein each of $R^b$, $R^c$ and $R^d$ is independently H or $C_1$-$C_6$ alkoxy. In one embodiment, $G^2$ is bis(4-methoxyphenyl)phenylmethyl (4,4'-dimethoxytrityl). In some such embodiments, $R^e$ is an unsubstituted or substituted $C_1$-$C_6$ alkyl. In one example, $R^e$ is 2-cyanoethyl (—CH$_2$CH$_2$CN). In some such embodiments, p is from 4 to about 50,000.

In some embodiments of the method described herein, the method further comprises blocking unreacted 5' hydroxyl group in the 5' unblocked first bioconjugate prior to step (b). In some such embodiment, said blocking is performed by reacting the 5' hydroxyl group with acetic anhydride (Ac$_2$O).

In some embodiments of the method described herein, the isolation and/or purification of the 5' unblocked second bioconjugate is achieved by a filtration or dialysis described herein. For example, the filtration may use a regenerated cellulose membrane described herein. In some embodiments, the regenerated cellulose membrane has a molecular weight cutoff (MWCO) from about 5 kDa to about 50 kDa, from about 6 kDa to about 40 kDa, about 7 kDa to about 30 kDa, or about 8 kDa to about 12 kDa. In some further embodiments, steps (a)-(d) are repeated multiple cycles until a desired length of oligonucleotide has been synthesized. In some such embodiments, the oligonucleotide synthesized may comprises at least 2, 3, 4, 5, 6, 7, 8, 9, 10, 11, 12, 13, 14, 15, 16, 17, 18, 19 or 20 bases.

In some embodiments, the method further comprises removing the synthesized oligonucleotides from the PVH. In some such embodiments, the removing step includes a step of covalent chemical bond scission. In some embodiments, the removing step includes hydrolysis. In certain embodiments, the removing includes hydrolysis at a temperature from about 0° C. to about 80° C., or about 10° C. to about 60° C., or about 15° C. to about 30° C.

Figure 5:
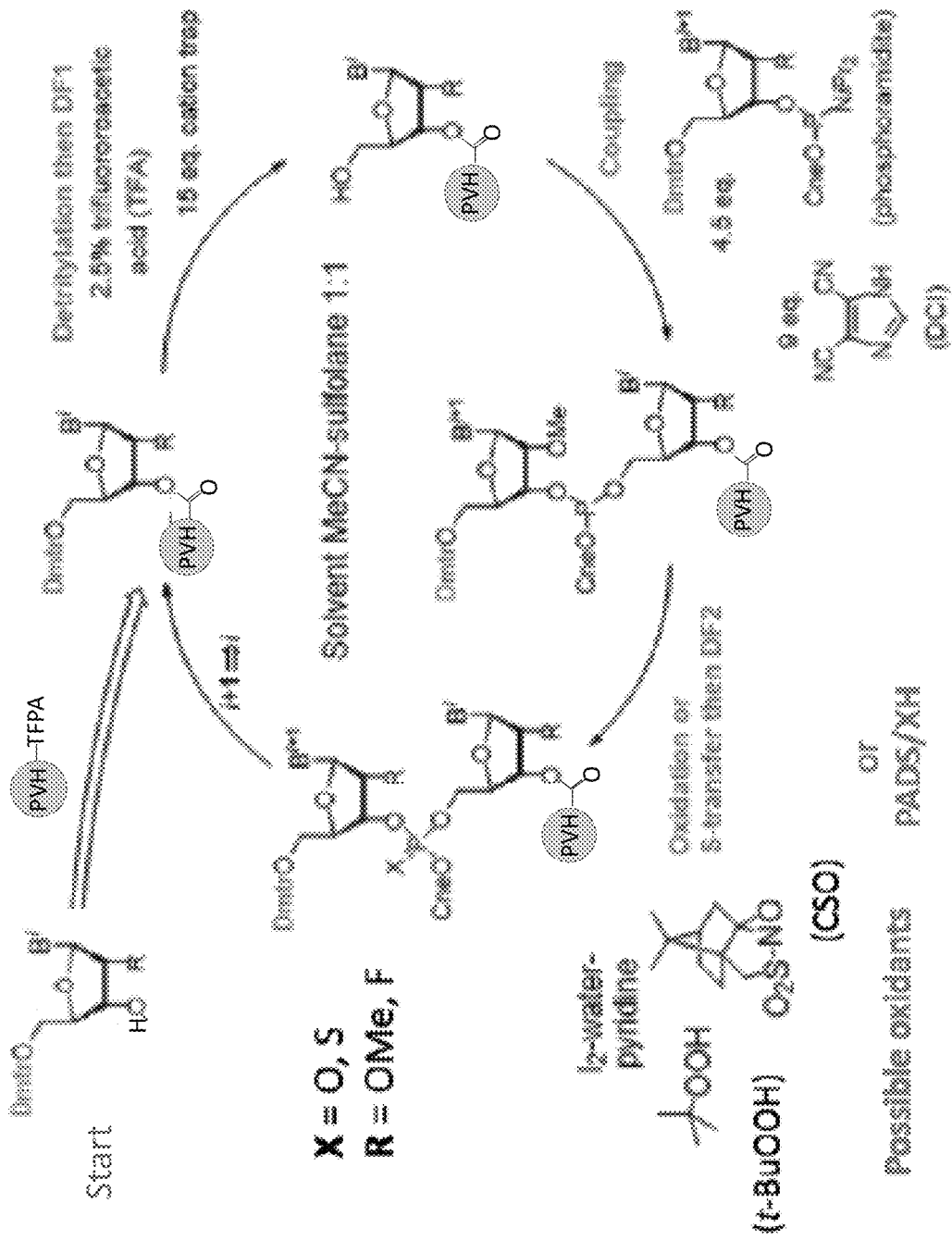
FIG. 5 is a reaction scheme of a first cycle of liquid phase oligonucleotide synthesis according to an embodiment of the present application.
Figure 6:
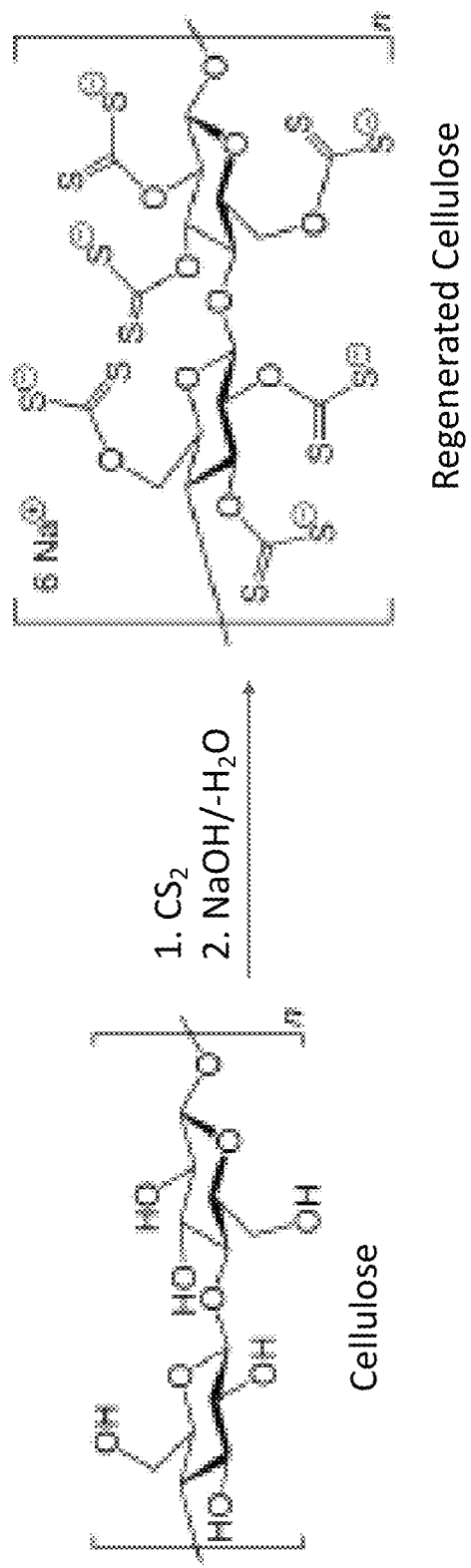
FIG. 6 is a reaction scheme for preparing a regenerated cellulose membrane for dialysis according to an embodiment of the present application.

A general reaction scheme of the liquid phase oligonucleotide synthesis is illustrated in FIG. 1. A more detailed reaction scheme according to an embodiment of the method described herein is illustrated in FIG. 5. In FIG. 5, the nucleoside analog has methoxy or fluoro substitution at the 2' position of the ribose ring. The same method may also be used for other types of nucleoside analogs where the corresponding R may be H (i.e., 2-deoxy ribose), or —OR$^a$ as described herein. A reaction scheme for preparing the regenerated cellulose is described in FIG. 6.

In some embodiments of the method described herein, each of the first solvent and the second solvent comprise one or more non-protic polar solvents, or combinations thereof. In some further embodiments, the one or more non-protic polar solvents comprise acetonitrile, tetrahydrofuran (THF), dimethylformamide (DMF), dimethyl sulfoxide (DMSO), dichloromethane (DCM), sulfolane, or combinations thereof. In one embodiment, the first solvent and/or the second solvent comprises acetonitrile. In another embodiment, the first solvent and/or the second solvent comprises a mixture of acetonitrile and sulfolane.

Polyvalent Polymer Hub (PVH) for Liquid Phase Oligonucleotide Synthesis

Some embodiments of the present application relate to PVH for liquid phase synthesis. In some embodiments, the liquid phase synthesis comprises liquid phase oligonucleotide synthesis, liquid phase peptide synthesis, liquid phase polynucleotide (i.e., nucleic acid), synthesis or liquid phase small molecule synthesis. In some embodiments, the PVH comprises or is a polymer for liquid phase oligonucleotide synthesis. The PVH is prepared from one or more monomers to produce the PVH having one or more repeating units. The monomers may include acrylic or methacrylic acid esters (e.g., acrylate) or combinations thereof, where certain acrylate monomers each contains a reactive ester group that allows for reaction with nucleoside or nucleotide analogs. The PVH may also contains repeating units of acrylic or methacrylic acid amides (e.g., acrylamide), or combination thereof. The PVH may comprise a linear polymer, a branched polymer, or star-shaped polymer, or combinations thereof. The PVH may comprise a homopolymer, a block copolymer, or a random copolymer, or combinations thereof.

In some embodiments, the PVH comprises a repeating unit of Formula (II) or (II'):

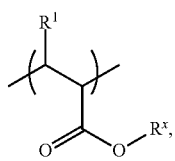

(II)

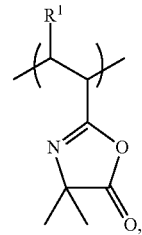

(II')

wherein $R^1$ is H or $C_1$-$C_6$ alkyl; $R^x$ is

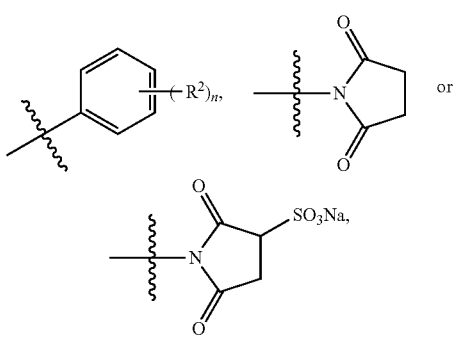

each $R^2$ is independently halogen, nitro or cyano; n is 1, 2, 3, 4, or 5; and wherein —OR$^x$ in Formula (II) is a leaving group for attaching a 3'-oxygen of a nucleoside or nucleotide analog to the carbonyl group. In some embodiments, $R^1$ is methyl, ethyl, propyl, butyl, pentyl or hexyl. In some embodiments, $R^1$ is H. In some embodiments, each $R^2$ is fluoro, chloro, nitro or cyano and n is 3, 4, or 5. In some embodiments, each $R^2$ is fluoro or chloro, and n is 3, 4, or 5. In some embodiments, each $R^2$ is fluoro and n is 3, 4, or 5. In some embodiments, each $R^2$ is chloro and n is 3, 4, or 5. In some embodiments, each $R^2$ is nitro and n is 3, 4, or 5. In some embodiments, each $R^2$ is cyano and n is 3, 4, or 5. In some embodiments, each $R^2$ is fluoro and n is 4. In some embodiments, each $R^2$ is fluoro and n is 5.

In some embodiments, the PVH comprises a second repeating unit of Formula (III):

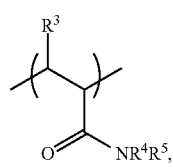

(III)

wherein $R^3$ is H or $C_1$-$C_6$ alkyl; and each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl. In some embodiments, $R^3$ is methyl, ethyl, propyl, butyl, pentyl or hexyl. In some embodiments, $R^3$ is H. In some embodiments, each $R^4$ and $R^5$ is independently unsubstituted $C_1$-$C_6$ alkyl. In some embodiments, each $R^4$ and $R^5$ is methyl. In some embodiments, $R^4$ and $R^5$ together with the nitrogen atom to which they are attached form a structure selected from

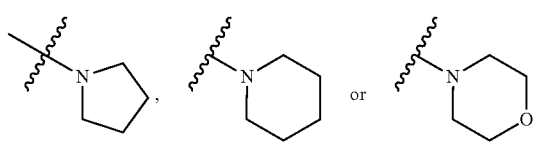

In further embodiments, the PVH comprises or is a copolymer, comprising one or more acrylate repeating units of Formula (II) or (II'), or a combination thereof, and one or more acrylamide repeating units of Formula (III) as described herein, comprising or having the structure:

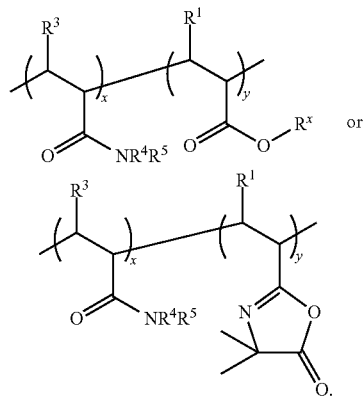

The copolymer may be a block copolymer or a random copolymer. In some embodiments, $R^1$ is H. In further embodiments, each of $R^4$ and $R^5$ is methyl. In some further embodiments, the PVH comprises or has the structure:

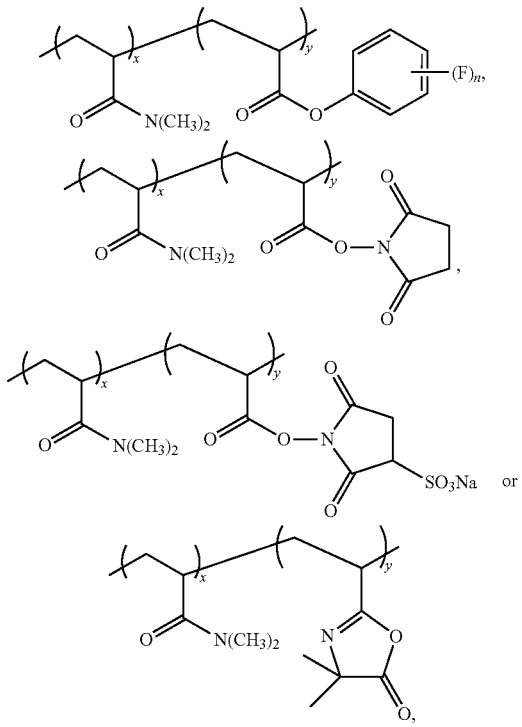

wherein x is an integer from 1 to 500,000; y is an integer from 1 to 500,000; and n is 4 or 5. In one embodiment, n is 4. In some further embodiments, x is an integer from 20 to 10,000 and y is an integer from 4 to 2,000. The ratio of x:y may range from about 1:1000 to about 1000 to 1, from about 1:500 to about 500:1, from about 1:200 to about 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, or from about 1:5 to about 5:1. In some embodiments, the acrylate repeating units (y) in the copolymer is from about 0.1 mol % to about 100 mol %, form about 1 mol % to about 80 mol %, from about 5 mol % to about 60 mol %, or from about 10 mol % to about 50 mol %. In further embodiments, the number of acrylate repeating units (i.e., y) in the PVH is at least 5, 10, 20, 30, 40, 50, 60, 70, 80, 90, 100, 200, 300, 400, 500, 600, 700, 800, 900, or 1000.

In one embodiment, the PVH comprises 2,3,5,6-tetrafluorophenyl acrylate (TFPA) and N,N-dimethyl acrylamide (DMA) wherein the PVH can be referred to with the abbreviation poly(TFPA-co-DMA), having the structure

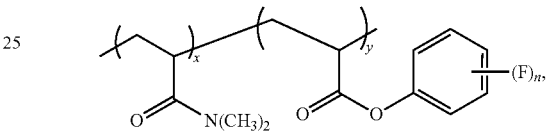

where n is 4. In some embodiments, the acrylate repeating units (y) in the copolymer is from about 0.1 mol % to about 100 mol %, form about 1 mol % to about 80 mol %, from about 5 mol % to about 60 mol %, or from about 10 mol % to about 50 mol %. In one embodiment, the acrylate repeating units is about 15 to 20 mol %, or about 18 mol %.

In any embodiments of the PVH described herein, the PVH has an average molecular weight from about 10 kDa to about 1000 kDa, or from about 20 kDa to about 500 kDa, or from about 30 kDa to about 100 kDa.

In any embodiments of the PVH described herein, the PVH may have a loading capacity of from about 10 μmol to about 600 μmol, from about 20 μmol to about 500 μmol, from about 30 μmol to about 400 μmol, or from about 40 μmol to about 300 μmol, per gram of PVH. In some further embodiments, the PVH has a loading capacity of about 10 μmol, 20 μmol, 30 μmol, 40 μmol, 50 μmol, 60 μmol, 70 μmol, 80 μmol, 90 μmol, 100 μmol, 150 μmol, 200 μmol, 250 μmol, 300 μmol, 350 μmol, 400 μmol, 450 μmol, 500 μmol, 550 μmol or 600 μmol per gram of PVH, or a range defined by any two of the preceding values.

In any embodiments of the PVH described herein, the PVH may be used in the liquid phase synthesis method described herein.

Polymeric Bioconjugates Prepared by LPOS

Some additional aspect of the present disclosure relates to a polymeric bioconjugate comprising one or more repeating units of Formula (V):

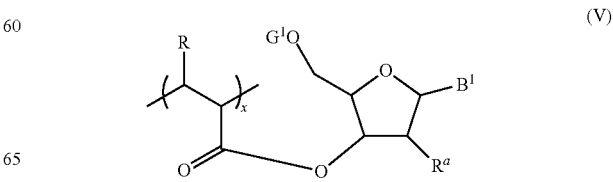

and optionally one or more repeating units of Formula (III)

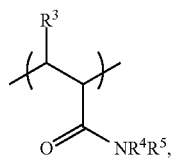
(III)

wherein
   each of $R^1$ and $R^3$ is independently H or $C_1$-$C_6$ alkyl;
   each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl;
   $B^1$ is a nitrogenous base described herein;
   $G^1$ is H or a 5' hydroxyl blocking group; and
   $R^a$ is —H, —OH, halogen, —O—($C_1$-$C_6$ alkyl), —O—($C_1$-$C_6$ haloalkyl), or —OX, where X is a 2' hydroxyl protecting group.

In some embodiments, the polymeric bioconjugate comprises or has the structure of Formula (Ia):

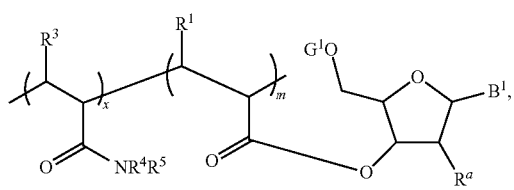
(Ia)

wherein each of x, and m is independently an integer from 1 to 500,000. In some embodiments, m is equal to less than y as described herein. In further embodiments, each of $R^1$ and $R^3$ is H. In further embodiments, each of $R^4$ and $R^5$ is methyl. In further embodiments, $G^1$ is H. In other embodiments, $G^1$ is

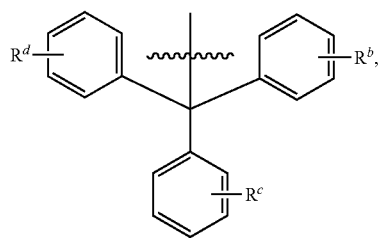

wherein each of $R^b$, $R^c$ and $R^d$ is independently H or $C_1$-$C_6$ alkoxy. In one embodiment, $G^1$ is 4,4'-dimethoxytrityl.

Additional aspect of the present disclosure relate to a polymeric bioconjugate, comprising one or more repeating units of Formula (VI), and optionally one or more repeating unit of Formula (III):

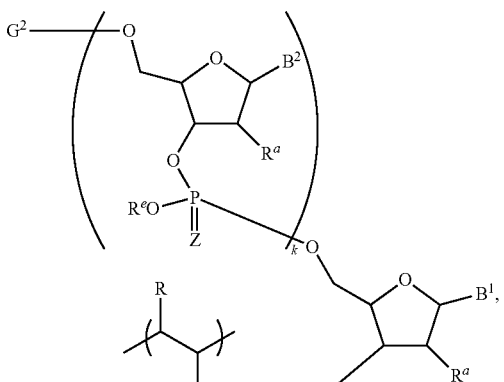
(VI)

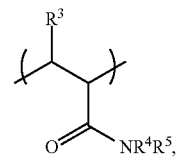
(III)

wherein
   each $R^1$ of $R^3$ is independently H or $C_1$-$C_6$ alkyl;
   each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl;
   $R^a$ is —H, —OH, halogen, —O—($C_1$-$C_6$ alkyl), —O—($C_1$-$C_6$ haloalkyl), or —OX, where X is a 2' hydroxyl protecting group.
   each of $B^1$ and $B^2$ is independently a nitrogenous base described herein;
   $G^2$ is a 5' hydroxyl blocking group;
   $R^e$ is unsubstituted or substituted $C_1$-$C_6$ alkyl;
   Z is O or S; and
   k is an integer from 1 to 500.

In further embodiments, the polymeric bioconjugate comprises or has the structure of Formula (Ib):

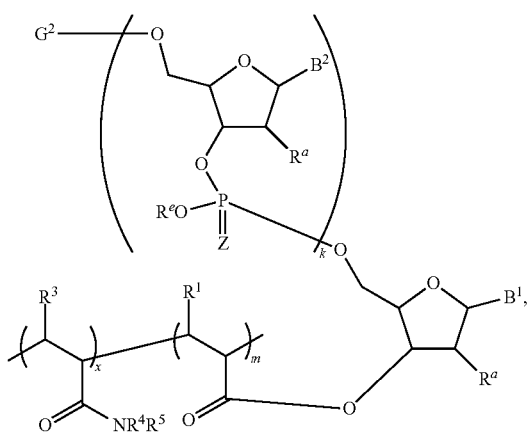
(Ib)

wherein each of x, and m is independently an integer from 1 to 500,000. In some embodiments, m is equal to less than y as described herein. In further embodiments, each of $R^1$ and $R^3$ is H. In further embodiments, each of $R^4$ and $R^5$ is methyl. In further embodiments, $G^2$ is H. In other embodiments, $G^2$ is

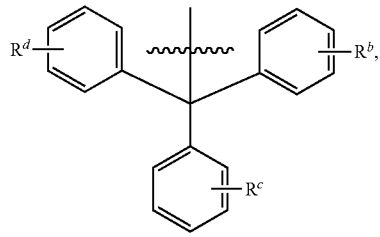

wherein each of $R^b$, $R^c$ and $R^d$ is independently H or $C_1$-$C_6$ alkoxy. In one embodiment, $G^2$ is 4,4'-dimethoxytrityl. In some embodiments, $R^e$ is substituted $C_1$-$C_6$ alkyl. In one example, $R^e$ is 2-cyanoethyl (—$CH_2CH_2CN$).

In any embodiments of the polymeric bioconjugates described herein, $B^2$ is independently optionally protected adenine, optionally protected deaza adenine, optionally protected cytosine, optionally protected guanine, optionally protected deaza guanine, optionally protected thymine, or optionally protected uracil. In further embodiments, $B^2$ is

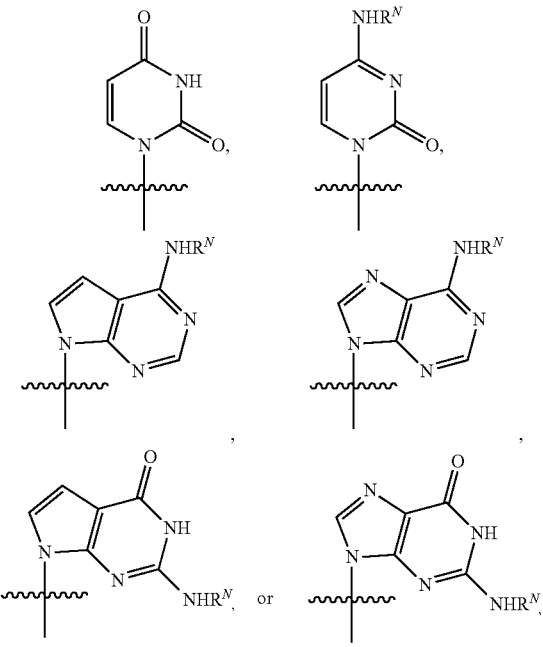

wherein $R^N$ is hydrogen, unsubstituted or substituted $C_1$-$C_6$ alkyl, or an amino protecting group, or the hydrogen in —$NHR^N$ is absent and $R^N$ is a divalent amino protecting group.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. Preparation of Poly(TFPA-co-DMA)

N,N-dimethyl acrylamide (DMA) obtained from Sigma Aldrich, and 2,3,5,6-tetrafluorophenyl acrylate (TFPA) obtained from Synquest Laboratories were purified by vacuum distillation prior to use. The initiator Vazo-52 [2,2'-azobis(2,4-dimethylvaleronitrile)] obtained from Combi-Blocks was used as received. A solution of about 5.39 g (24.49 mmol) of TFPA, about 4.51 g (45.49 mmol) of DMA, and about 0.05 g (0.2 mmol) of Vazo-52 in 30 mL of anhydrous acetonitrile (AcN) was purged with ultrapure argon for about 30 minutes at a flow rate of 60 mL/min and constant mechanically stirring with a 1-inch half-moon-shape Teflon blade at 200 rpm. The reaction flask was then lowered into a 55° C. oil-bath while having constant stirring but reduced argon flow of 15-20 mL/min. The polymerization was conducted under these conditions for 6 hours. At the end of 6 hours, the reaction mixture was cooled to ambient temperature in open air. The AcN and residual monomers were removed under reduced pressure in a Rota-Vap at 55° C. water-bath temperature. The polymer product was re-dissolved in 30 mL of anhydrous tetrahydrofuran (THF) at 55° C. To the THF solution, about 30 mL of anhydrous hexane was added dropwise under argon with magnetic stirring until a cloudy suspension was obtained. The cloudy suspension was then added into 800 mL of anhydrous hexane in a 2-L Erlenmeyer flask through a 22-gauge syringe needle in a fine stream under argon while mechanically stirred at about 150 rpm with a 2-inch Teflon stirring blade. The precipitated polymer was stirred for an additional 5 minutes under argon. The hexane was discarded, and 500 mL of fresh anhydrous hexane was added and mechanically stirred gently for another 15 minutes under argon. The poly(TFPA-co-DMA) product in coarse fibers was then transferred into a large mouth 500-mL glass jar and dried under vacuum at 55° C. for 24 hours. The TFPA proportion in the poly(TFPA-co-DMA) product was determined to be 18 mol % by $^1$H NMR analysis.

Example 2. Dialysis of Poly(TFPA-co-DMA)

A solution of 312.8 mg of poly(TFPA-co-DMA) prepared in Example 1 and 10.0 mL of anhydrous AcN was prepared and transferred into a dialysis tube having a length of 10 cm. The dialysis tube (Spectra/Por-7 Dialysis membrane, 15 KDa MWCO, 2.4 cm flat width, 1.5 cm diameter, and 1.8 mL/cm capacity) was immersed into a dialysis bath containing 200.0 mL AcN as a dialysis solvent. Dialysis was conducted for 24 h and afterward the dialysis tube was separated from the dialysis bath.

The solution in the dialysis tube was transferred to a recovery flask and the dialysis tube was rinsed with AcN. The solution and rinsings were combined and the AcN in the recovery flask was removed by a Rota-Vap at 50 mbar. The residue was subjected to vacuum drying and 282.70 mg of poly(TFPA-co-DMA) (90.4%) was observed in the dialysis tube as shown in Table 1. Dialysis using a membrane having an MWCO of 15 KDa retained more than 90% poly(TFPA-co-DMA) in the dialysis tube.

The dialysis solvent was transferred into a recovery flask and the dialysis bath was rinsed with AcN. The dialysis solvent and rinsings were combined and the AcN in the recovery flask was removed by a Rota-Vap at 50 mbar. The recovery flask was rinsed with two 10 mL portions of water and the water-clear rinsings were concentrated under vacuum to recover 1.50 mg of the PVH copolymer as shown in Table 1.

Example 3. Dialysis of 5'-O-DMT-dT

The procedure of Example 2 was followed using 218.7 mg of 5'-O-DMT-dT (Hongene Biotech, MW=544.49) in place of poly(TFPA-co-DMA). An amount of 196.70 mg of 5'-O-DMT-dT (90%) was observed in the dialysis bath as shown in Table 1. Dialysis using a membrane having an MWCO of 15 KDa transferred 90% of the 5'-O-DMT-dT from the dialysis tube into the dialysis bath.

TABLE 1

| Example | poly(TFPA-co-DMA) (mg) | 5'-O-DMT-dT (mg) | Recovery from dialysis bath (mg) | Recovery from dialysis tube (mg) | Polymer retained (%) | dT excluded (%) |
|---|---|---|---|---|---|---|
| 2 | 312.8 | — | 1.50 | 282.70 | 90.4 | — |
| 3 | — | 218.7 | 196.70 | 10.10 | — | 90.0 |
| 4 | 320.0 | 226.2 | Not determined | 284.90 | Not determined | Not determined |

Example 4: Bioconjugated 5'-O-DMT-dT onto Poly(TFPA-co-DMA)

Figure 2:
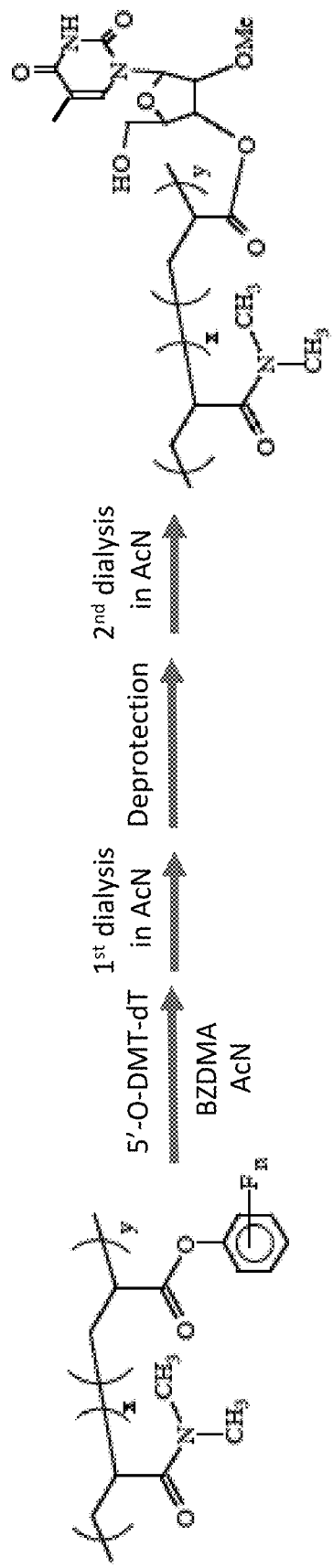
FIG. 2 is a reaction scheme of the reaction between 5'-O-DMT-dT and a polymer for liquid phase oligonucleotide synthesis followed by removal of the DMT group according to an embodiment of the present application.

Transferred 320.0 mg of poly(TFPA-co-DMA) prepared in Example 1 and 226.2 mg of 5'-O-DMT-dT into a 100-mL round bottom flask, and 10 mL of anhydrous AcN was added to dissolve under mild magnetic stirring. The solution was purged with argon with constant gentle magnetic stirring at 35° C. for 15 minutes. To the purged solution 0.1 mL of N,N-dimethyl benzylamine (TCI) was added with a syringe needle. The reaction was allowed to proceed for 20 hours at ambient temperature. A white powdery precipitate was observed. The reaction solution was warmed in an oil bath at 30° C. for 60 minutes to give a clear solution. It was then transferred into the dialysis tube 18 cm in length (15 KDa MWCO, 2.4 cm flat width, 1.5 cm diameter, and 1.8 mL/cm capacity) and immersed into 400 mL of AcN. The dialysis was allowed to proceed for 23 hours with one change of 400 mL can (a total of 800 mL of AcN). The reaction solution in the dialysis tube was transferred into a 100-mL round bottom flask. The dialysis tube was rinsed with two 10-mL aliquots of can and the rinsings were added into the 100-mL flask. The AcN was removed by Rota-Vap, and the residue was dried by vacuum to give 284.90 mg of the DMT-dT conjugated poly(TFPA-co-DMA). FIG. 2 illustrates the steps of (i) reaction between 5'-O-DMT-dT and poly(TFPA-co-DMA), (ii) a first dialysis; (iii) removal of the DMT group; and (iv) a second dialysis.

Figure 3A:
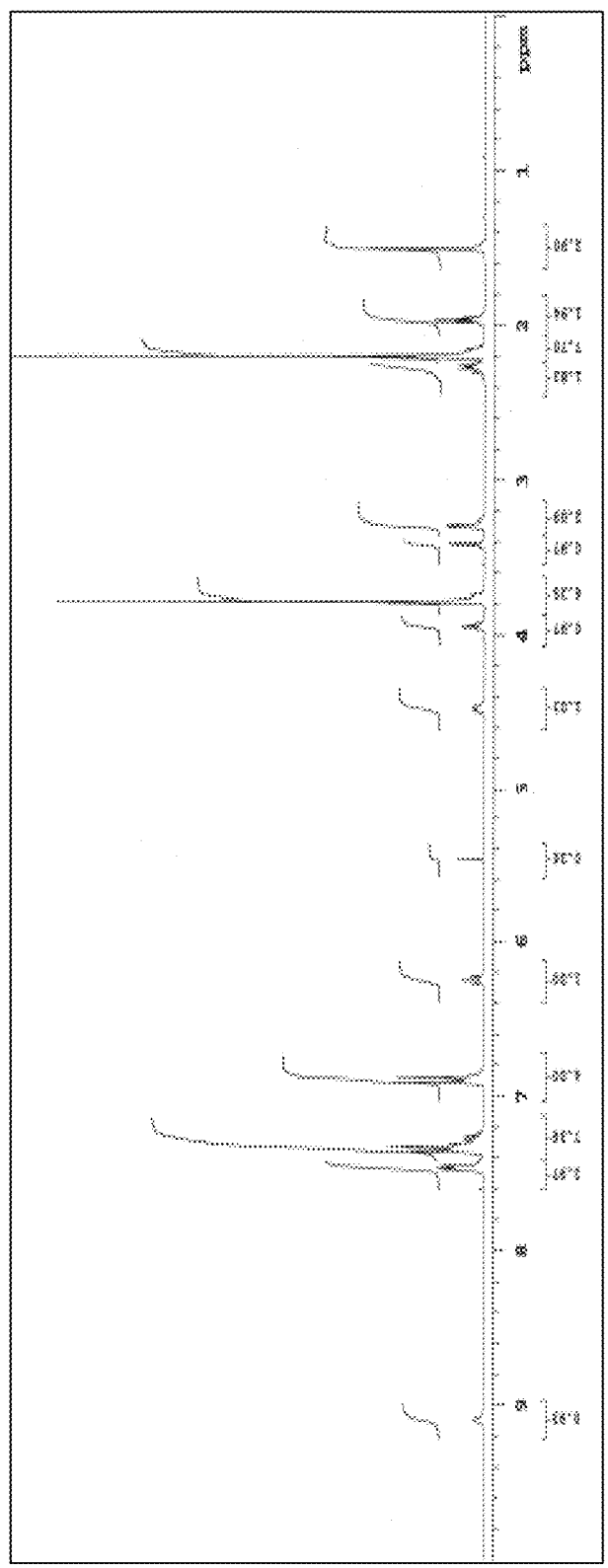
FIG. 3A is a $^1$H NMR spectrum measured in $CD_3CN$ of 5'-O-DMT-dT.
Figure 3B:
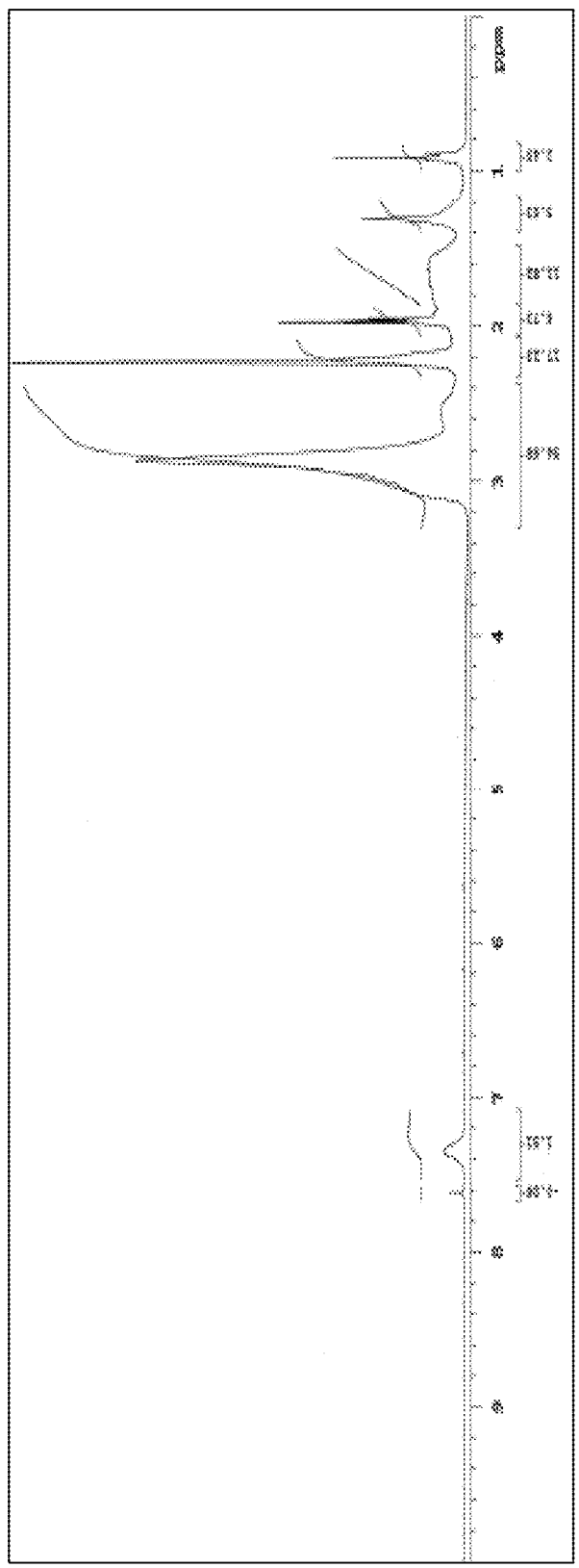
FIG. 3B is a $^1$H NMR spectrum measured in $CD_3CN$ of a poly(TFPA-co-DMA) according to an embodiment of the present application.
Figure 3C:
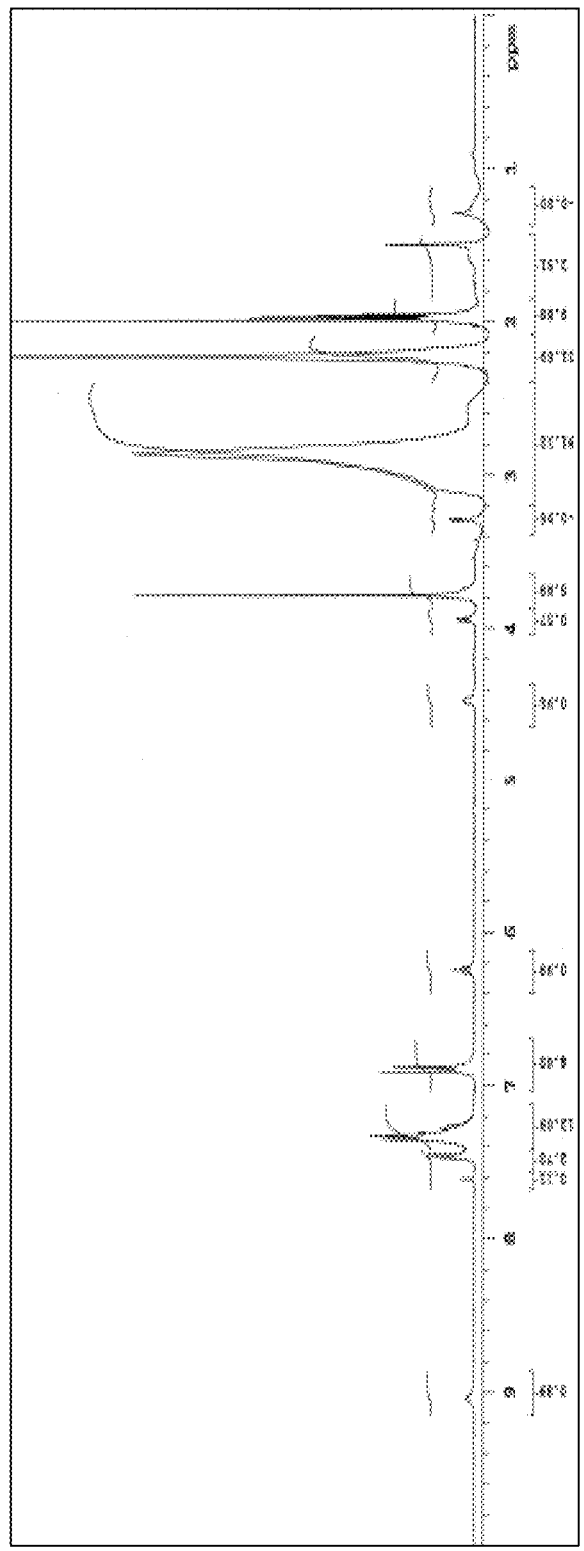
FIG. 3C is a $^1$H NMR spectrum measured in $CD_3CN$ of a DMT-dT conjugated poly(TFPA-co-DMA) according to an embodiment of the present application.

FIGS. 3A, 3B and 3C illustrate $^1$H NMR spectra taken in AcN-d3 for 5'-O-DMT-dT, the poly(TFPA-co-DMA) prepared in Example 1 and the DMT-dT conjugated poly(TFPA-co-DMA) prepared in Example 4, respectively. Comparison of the $^1$H NMR integrations of various signals indicates that 5'-O-DMT-dT had been conjugated on the PVH. After being subjected to two dialysis exchanges in a 400 mL of AcN dialysis bath, the maximum amount of free 5'-O-DMT-dT in a 15-mg sample of the DMT-dT conjugated poly(TFPA-co-DMA) prepared for NMR spectroscopy is 0.007 mg, which under the detection limit of NMR instrumentation.

Example 5. UV/Vis Analysis of DMT Loading of the DMT-dT Conjugated PVH

Figure 4:
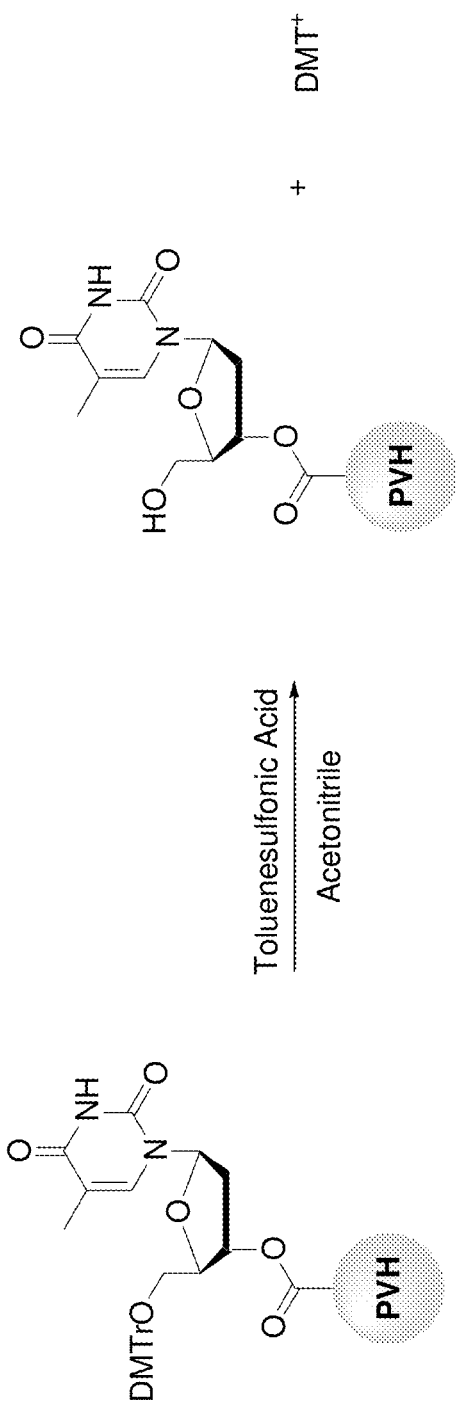
FIG. 4 is a reaction scheme of the removal of DMT from a DMT-dT conjugated poly(TFPA-co-DMA) according to an embodiment of the present application.

DMT-dT loading of the DMT-dT conjugated poly(TFPA-co-DMA) was determined by UV/Vis spectrophotometry. The DMT group is removed from dT under acidic hydrolysis as shown in FIG. 4 and the loading of DMT-dT was quantitatively determined. An aliquot of 2.20 mg of the DMT-dT conjugated poly(TFPA-co-DMA) prepared in Example 4 was washed with 100 mL of AcN containing 0.46 M toluenesulfonic acid (TSA-AcN). A blank UV/Vis spectrum of 0.46 M TSA-AcN solution was acquired. An aliquot of the supernatant from the washing solution was transferred to a dry cuvette and UV/VIS scanning was performed. The DMT-dT loading on the DMT-dT conjugated poly(TFPA-co-DMA) was determined from an absorbance value (A) of 0.59674 at 498 nm with a sample volume of 100 mL. The extinction coefficient ε for DMT was estimated 76.5 mL/cm*μmole. Using the equation: DMT-dT loading (μmole/g)=[A*sample volume (mL)]/[76.5 (mL*cm$^{-1}$*μmole$^{-1}$)*sample weight (g)]

DMT-dT loading of the DMT-dT conjugated poly(TFPA-co-DMA) was calculated to be 355 μmol/g.

While the present application has been described with reference to the specific embodiments thereof, it should be understood by those skilled in the art that various changes may be made, and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

What is claimed is:

1. A method for making an oligonucleotide by liquid phase oligonucleotide synthesis, comprising:
   dissolving a polyvalent hub (PVH) in a first solvent to form a reaction matrix, wherein the PVH comprises a copolymer of acrylate polymer and acrylamide polymer, and the acrylate polymer of the PVH have a plurality of reactive ester groups capable of reacting with nucleoside or nucleotide analogs; and
   contacting the PVH with one or more nucleoside analogs to form a first bioconjugate comprising a structure of Formula (I):

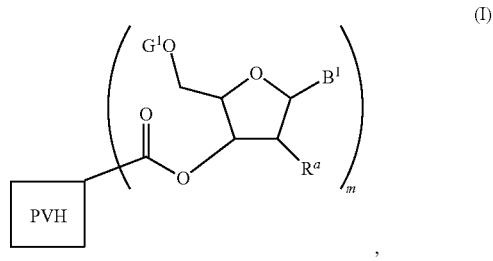

wherein
   B$^1$ is a nitrogenous base;
   G$^1$ is a 5' hydroxyl blocking group;
   R$^a$ is —H, —OH, halogen, —O—(C$_1$-C$_6$ alkyl), —O—(C$_1$-C$_6$ haloalkyl), or —OX, where X is a 2' hydroxyl protecting group; and
   m is an integer from 1 to 500,000.

2. The method of claim 1, wherein $B^1$ is independently optionally protected adenine, optionally protected deaza adenine, optionally protected cytosine, optionally protected guanine, optionally protected deaza guanine, optionally protected thymine, or optionally protected uracil.

3. The method of claim 2, wherein $B^1$ is

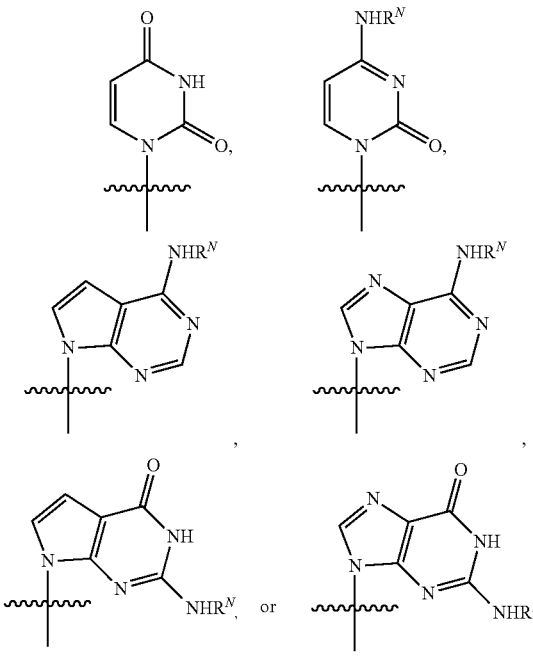

wherein $R^N$ is hydrogen, unsubstituted or substituted $C_1$-$C_6$ alkyl, or an amino protecting group, or the hydrogen in —NHR$^N$ is absent and R$^N$ is a divalent amino protecting group.

4. The method of claim 1, wherein each $G^1$ is independently a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

5. The method of claim 1, wherein each reactive ester group of the PVH independently comprises —C(=O)OEW, NHS ester, sulfo NHS ester, or

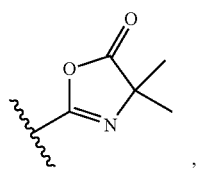 [SMILES: *C1=NC(C)(C)C(=O)O1]

wherein EW is an electron-withdrawing group.

6. The method of claim 1, wherein the PVH has an average molecular weight from about 10 kDa to about 1000 kDa, or from about 30 kDa to about 100 kDa.

7. The method of claim 1, wherein the acrylate polymer comprises a plurality of repeating units of Formula (II) or (II'), or a combination thereof:

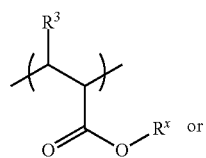
(II)

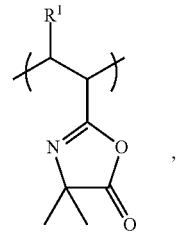
(II')

wherein
$R^1$ is H or $C_1$-$C_6$ alkyl;
$R^x$ is

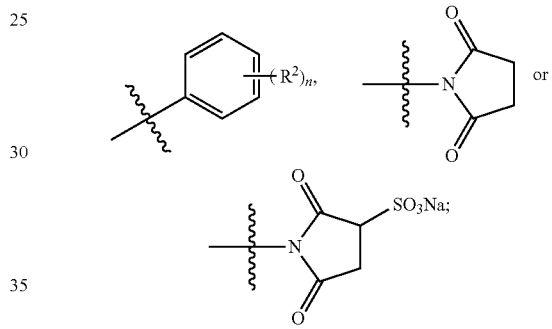

each $R^2$ is independently halogen, nitro or cyano; and
n is 1, 2, 3, 4, or 5.

8. The method of claim 7, wherein $R^1$ is H.

9. The method of claim 7, wherein the acrylate polymer comprises repeating units of Formula (IIa):

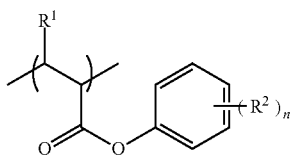

each $R^2$ is fluoro, and n is 3, 4, or 5.

10. The method of claim 1, wherein the acrylamide polymer comprises a plurality of repeating units of Formula (III):

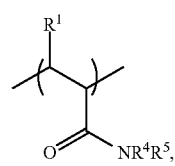
(III)

wherein $R^3$ is H or $C_1$-$C_6$ alkyl; and each of $R^4$ and $R^5$ is independently H, unsubstituted or substituted $C_1$-$C_6$ alkyl, unsubstituted or substituted phenyl, or $R^4$ and $R^5$ together with the nitrogen atom to which they are attached form an optionally substituted 5 or 6 membered heterocyclyl.

11. The method of claim 10, wherein $R^3$ is H and each $R^4$ and $R^5$ is independently unsubstituted $C_1$-$C_6$ alkyl.

12. The method of claim 1, wherein the molar ratio of the acrylate polymer to the acrylamide polymer in the copolymer is from about 1:200 to about 200:1, from about 1:100 to about 100:1, from about 1:90 to about 90:1, from about 1:80 to about 80:1, from about 1:70 to about 70:1, from about 1:60 to about 60:1, from about 1:50 to about 50:1, from about 1:20 to about 20:1, from about 1:10 to about 10:1, from about 1:5 to about 5:1, from about 1:2 to about 2:1, or about 1:1.

13. The method of claim 1, wherein the PVH comprises the structure:

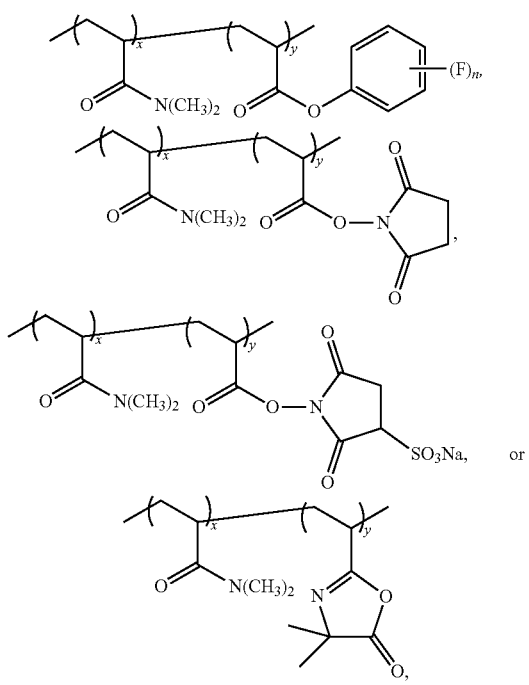

wherein x is an integer from 1 to 500,000;
y is an integer from 1 to 500,000; and
n is 4 or 5.

14. The method of claim 13, wherein the first bioconjugate comprises the structure of Formula (Ia):

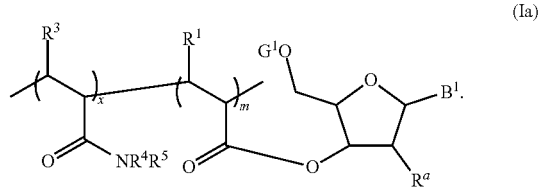

15. The method of claim 1, further comprising:
removing the 5' blocking group ($G^1$) to form a 5' unblocked first bioconjugate; and
isolating the 5' unblocked first bioconjugate;
wherein the 5' unblocked first bioconjugate comprises the structure of Formula (I'):

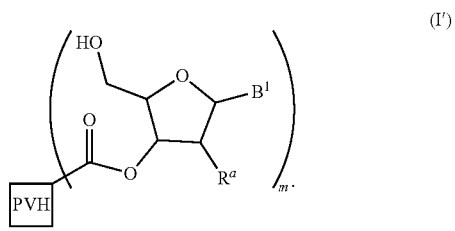

16. The method of claim 15, wherein the 5' unblocked bioconjugate comprises the structure of Formula (Ia'):

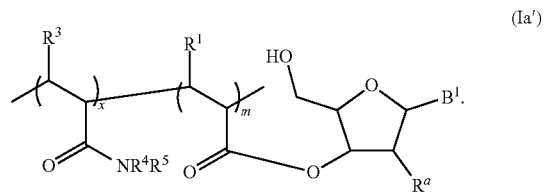

17. The method of claim 16, wherein both $R^1$ and $R^3$ is H, and each $R^4$ and $R^5$ is methyl.

18. The method of claim 15, wherein said isolation of the 5' unblocked first bioconjugate is achieved by dialysis or ultrafiltration.

19. The method of claim 18, wherein the dialysis is performed with a membrane comprising a regenerated cellulose having a molecular weight cutoff (MWCO) from about 5 kDa to about 50 kDa.

20. The method of claim 15, further comprising:
(a) reacting the 5' unblocked first bioconjugate with one or more nucleoside phosphoramidite analogs in a second solvent to form a second bioconjugate comprising the structure of Formula (IV):

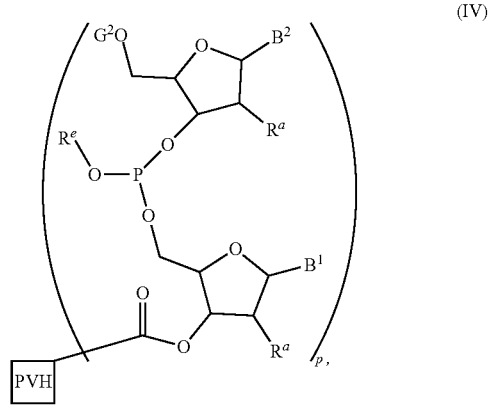

wherein
$G^2$ is a 5' hydroxyl blocking group;
$B^2$ is a nitrogenous base;
$R^e$ is a phosphite protecting group; and
p is an integer of 1 to 500,000;
(b) oxidizing the phosphite moiety in Formula (IV);

(c) removing the 5' blocking group G² to form a 5' unblocked second bioconjugate comprising the structure of Formula (IV'):

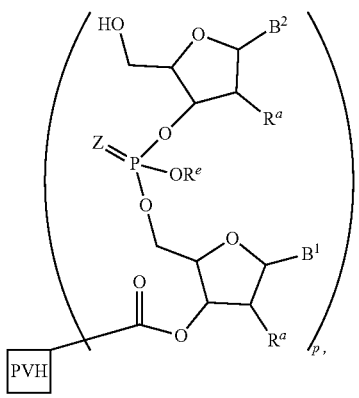

wherein

Z is O or S; and (d) isolating the 5' unblocked second bioconjugate.

21. The method of claim 20, further comprising blocking unreacted 5' hydroxyl group in the 5' unblocked first bioconjugate prior to step (b).

22. The method of claim 20, wherein B² is independently optionally protected adenine, optionally protected deaza adenine, optionally protected cytosine, optionally protected guanine, optionally protected deaza guanine, optionally protected thymine, or optionally protected uracil.

23. The method of claim 22, wherein B² is

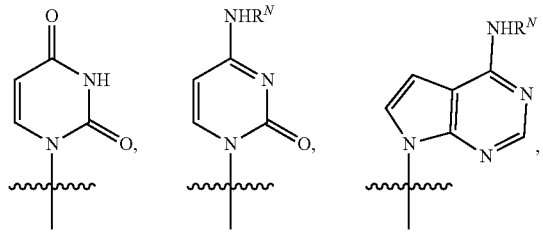

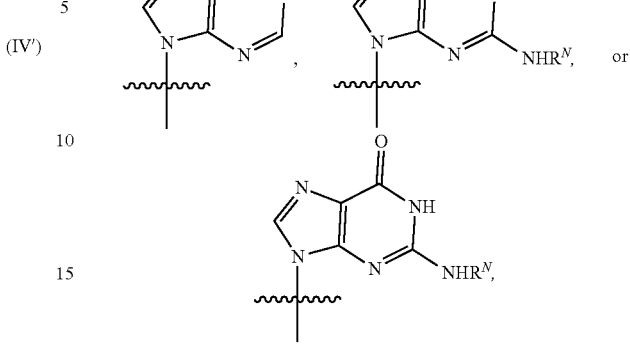

wherein $R^N$ is hydrogen, unsubstituted or substituted $C_1$-$C_6$ alkyl, or an amino protecting group, or the hydrogen in —$NHR^N$ is absent and $R^N$ is a divalent amino protecting group.

24. The method of claim 20, wherein each G² is independently a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl, and 9-(4-methoxyphenyl)xanthen-9-yl.

25. The method of claim 20, wherein $R^e$ is —$CH_2CH_2CN$.

26. The method of claim 20, wherein said isolation of the 5' unblocked second bioconjugate is achieved by filtration or dialysis.

27. The method of claim 20, wherein steps (a)-(d) are repeated multiple cycles until a desired length of oligonucleotide has been synthesized.

28. The method of claim 27, further comprising removing the oligonucleotides from the PVH.

29. The method of claim 20, wherein each of the first solvent and the second solvent comprise one or more non-protic polar solvents, or combinations thereof.

30. The method of claim 29, wherein the one or more non-protic polar solvents comprise acetonitrile, tetrahydrofuran (THF), dimethylformamide (DMF), dimethyl sulfoxide (DMSO), dichloromethane (DCM), sulfolane, or combinations thereof.

31. The method of claim 1, wherein the formation of the first bioconjugate does not require a succinate linker to attach the nucleoside analog to the PVH.

* * * * *

UNITED STATES PATENT AND TRADEMARK OFFICE
CERTIFICATE OF CORRECTION

PATENT NO. : 11,725,073 B2
APPLICATION NO. : 17/562714
DATED : August 15, 2023
INVENTOR(S) : Aldrich N. K. Lau et al.

Page 1 of 3

It is certified that error appears in the above-identified patent and that said Letters Patent is hereby corrected as shown below:

In the Specification

Column 3, Lines 33-52 (approx.), delete " 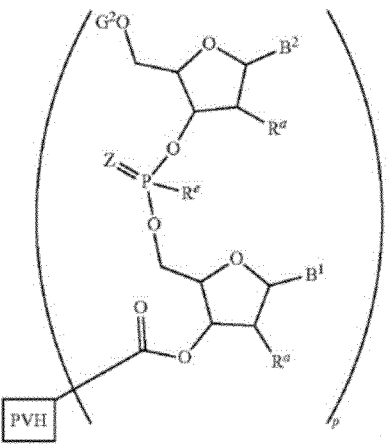 " and insert 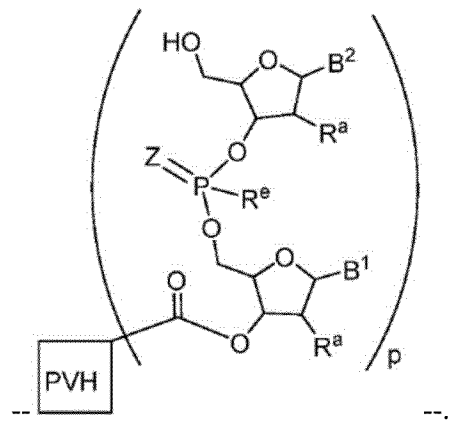 --.

Signed and Sealed this
Twenty-first Day of May, 2024

Katherine Kelly Vidal
*Director of the United States Patent and Trademark Office*

CERTIFICATE OF CORRECTION (continued)
U.S. Pat. No. 11,725,073 B2

Column 4, Lines 48-55 (approx.), delete " 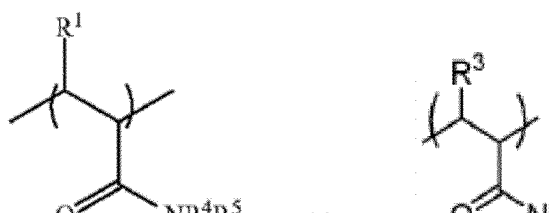 " and insert --.

Column 16, Line 53 (approx.), delete "form" and insert -- from --.

Column 17, Line 6, delete "form" and insert -- from --.

Column 24, Line 11, delete "form" and insert -- from --.

Column 24, Line 32, delete "form" and insert -- from --.

Column 24, Lines 59-66 (approx.), delete " 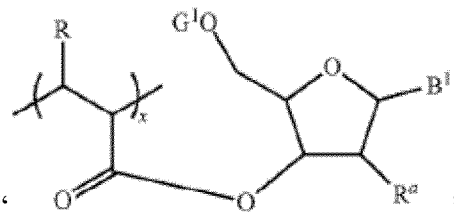 " and insert

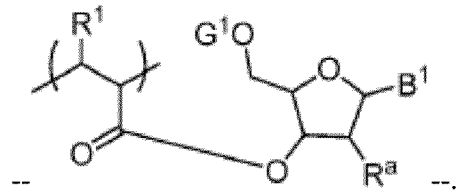 --.

Column 26, Line 1-8 (approx.), delete " 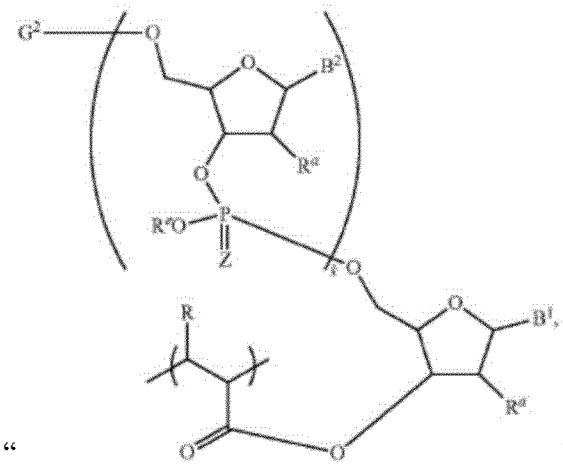 " and insert

CERTIFICATE OF CORRECTION (continued)
U.S. Pat. No. 11,725,073 B2

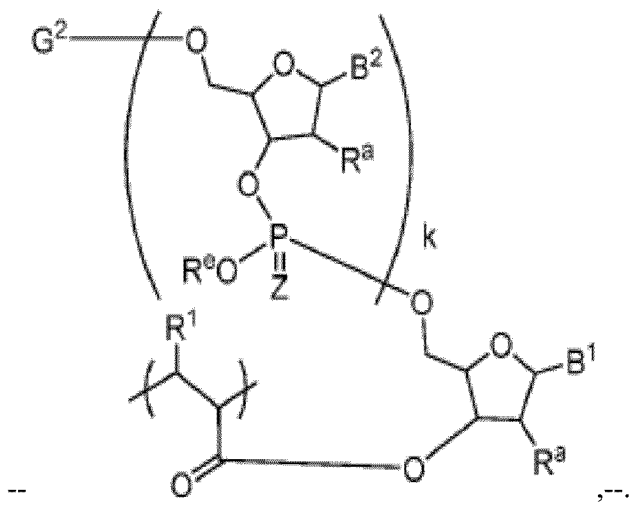

In the Claims

Column 32, Lines 2-9 (approx.), Claim 7, delete " 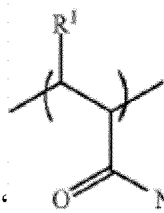 " and insert -- 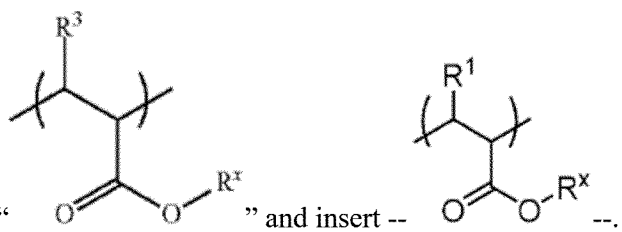 --.

Column 32, Line 59-65 (approx.), Claim 10, delete " 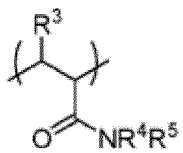 " and insert
-- 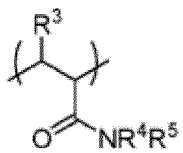 ,--.